(12) United States Patent
Reed et al.

(10) Patent No.: US 12,065,449 B2
(45) Date of Patent: Aug. 20, 2024

(54) FLUORESCENT PROANTHOCYANIDINS

(71) Applicant: SYNESIS LLC, Wisconsin Rapids, WI (US)

(72) Inventors: Jess D. Reed, Verona, WI (US); Daniel Alfredo Esquivel-Alvarado, Wisconsin Rapids, WI (US); Emilia Alfaro-Viquez, Wisconsin Rapids, WI (US); Christian G. Krueger, Cambridge, WI (US)

(73) Assignee: Synesis LLC, Wisconsin Rapids, WI (US)

( * ) Notice: Subject to any disclaimer, the term of this patent is extended or adjusted under 35 U.S.C. 154(b) by 0 days.

(21) Appl. No.: 18/547,958

(22) PCT Filed: Feb. 24, 2022

(86) PCT No.: PCT/US2022/017658
§ 371 (c)(1),
(2) Date: Aug. 25, 2023

(87) PCT Pub. No.: WO2022/182843
PCT Pub. Date: Sep. 1, 2022

(65) Prior Publication Data
US 2024/0059713 A1    Feb. 22, 2024

Related U.S. Application Data

(60) Provisional application No. 63/153,662, filed on Feb. 25, 2021.

(51) Int. Cl.
| | |
|---|---|
| A61K 9/20 | (2006.01) |
| A61K 9/00 | (2006.01) |
| A61K 9/06 | (2006.01) |
| A61K 9/12 | (2006.01) |
| A61K 9/48 | (2006.01) |
| C07D 519/00 | (2006.01) |
| G01N 33/569 | (2006.01) |

(52) U.S. Cl.
CPC .......... *C07D 519/00* (2013.01); *A61K 9/0019* (2013.01); *A61K 9/06* (2013.01); *A61K 9/124* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/485* (2013.01); *A61K 9/4858* (2013.01); *A61K 9/4866* (2013.01); *G01N 33/56916* (2013.01); *G01N 2333/245* (2013.01); *G01N 2469/10* (2013.01)

(58) Field of Classification Search
CPC ...... A61K 9/4866; A61K 9/2013; A61K 9/06; C07D 519/00
See application file for complete search history.

(56) References Cited

U.S. PATENT DOCUMENTS

2011/0059162 A1    3/2011   Reed et al.
2018/0000853 A1*   1/2018   Shapland ............... A61K 45/06

OTHER PUBLICATIONS

De Freitas et al., "Synthesis of a new catechin-pyrylium derived pigment", Tetrahedron Letters, 45, 9349-9352, Oct. 2004.
Esquivel Alvarado, "Matrix-Assisted Laser Desorption/Ionization Time-Of-Flight Mass Spectrometry for Characterizing Proanthocyanidins: Authenticity, Standardization, and Efficacy," Dissertation—University of Wisconsin-Madison, Oct. 2020, 30pgs.
Esquivel-Alvarado, et al., "Synthesis of Fluorescent Proanthocyanidin-Cinnamaldehydes Pyrylium Products for Microscopic Detection of Interactions with Extra-Intestinal Pathogenic *Escherichia coli*", J. Agric. Food Chem., 69, 10700-10708, Aug. 2021.
International Search Report and Written Opinion of the ISA/US dated Jun. 15, 2022 in International Application No. PCT/US2022/017658; 13pgs.
Li et al., "The DMACA-HCl Protocol and the Threshold Proanthocyanidin Content for Bloat Safety in Forage Legumes", J. Sci. Food Agric., 70, 89-101, Jan. 1996.
Sousa et al., "Preliminary Study of Oaklins, a New Class of Brick-Red Catechinpyrylium Pigments Resulting from the Reaction between Catechin and Wood Aldehydes", J. Agric. Food Chem., 53, 9249-9256, Oct. 2005.
Tanaka et al., "Structure of Polymeric Polyphenols of Cinnamon Bark Deduced from Condensation Products of Cinnamaldehyde with Catechin and Procyanidins", J. Agric. Food Chem., 56, 5864-5870, Jun. 2008.
Treutter, D., "Chemical Reaction Detection of Catechins and Proanthocyanidins with 4-Dimethylaminocinnamaldehyde", J. Chromatography, 467, 185-193, 1989.
Wallace et al., "Evaluation of Parameters that Affect the 4-Dimethylaminocinnamaldehyde Assay for Flavanols and Proanthocyanidins", J. Food Sci., 75(7):C619-25, Sep. 2010.

* cited by examiner

*Primary Examiner* — Gregory Listvoyb
(74) *Attorney, Agent, or Firm* — Haukaas Fortius PLLC; Michael Haukaas

(57) ABSTRACT

Proanthocyanidin-cinnamaldehydes pyrylium products (FP) were synthesized by the condensation reaction of proanthocyanidins (PAC) with various cinnamaldehydes. Synthesized FP exhibited fluorescence at higher excitation and emission wavelengths than PAC. FP were evaluated for their ability to agglutinate extra-intestinal pathogenic *Escherichia coli* (ExPEC). Results showed that FP were significantly more bioactive (p-value<0.05) for agglutinating ExPEC compared to PAC. Scanning electron microscopy indicates that FP interacts with ExPEC surface structures and suggests that FP have higher affinity with the fimbriae-like structures on the surface of ExPEC in comparison to PAC. In addition, fluorescent microscopy performed on in vitro and in vivo agglutination assays show that FP entrap ExPEC in a web-like network, thus demonstrating agglutination of ExPEC. Fluorescent proanthocyanidins offer a new approach to visualize bacterial infections and to treat such infections.

7 Claims, 17 Drawing Sheets

A.

B.

B.

FLUORESCENT PROANTHOCYANIDINS

RELATED APPLICATIONS

This application is a National Stage filing under 35 U.S.C. § 371 of International Application No. PCT/US2022/017658 filed Feb. 24, 2022, which claims the benefit of U.S. Provisional Patent Application No. 63/153,662, filed Feb. 25, 2021, which applications are incorporated herein by reference.

BACKGROUND OF THE INVENTION

Proanthocyanidins (PAC) are oligomers of flavan-3-ol units, which are associated with health benefits. PAC are linked by A- and B-type interflavan bonds. In A-type interflavan bonds, the flavan-3-ols form two bonds between $C_4$-$C_8$ and $C_2$—O—$C_7$, whereas in B-type interflavan bonds, the flavan-3-ols form only one bond between $C_4$-$C_8$. The structural heterogeneity of PAC is caused by their degree of polymerization (DP), the nature of their interflavan bonds (A- and B-type), the pattern of hydroxylation of their flavan units (B-ring), and their stereochemistry.

Visualization of temporal and dynamic interactions of PAC with bacteria using fluorescent microscopy would be a useful tool to test hypotheses regarding structure/function relationships in antimicrobial activity. However, the fluorescent properties of PAC are not useful for microscopy because excitation and emission wavelengths are located in the ultraviolet region. Our laboratory has previously published the use of 5-([4,6-dichlorotriazin-2-yl]amino)fluorescein (DTAF) to tag PAC. Unfortunately, auto-fluorescence at the excitation wavelength of fluorescein creates difficulties in distinguishing signal from noise in fluorescent microscopy using DTAF tagged PAC.

Cinnamaldehydes, such as cinnamaldehyde (CIN), 4-methylcinnamaldehyde (TOL), 4-(dimethylamino)cinnamaldehyde (DMAC), 4-hydroxy-3,5-dimethoxycinnamaldehyde (SIN), and 4-hydroxy-3-methoxycinnamaldehyde (CON) react with flavan-3-ols. Therefore, the condensation of a proanthocyanidin and a cinnamaldehyde provide new compounds that have fluorescence at useful wavelengths for understanding antimicrobial activity.

Accordingly, fluorescent proanthocyanidins offer a new approach to visualize bacterial infections and to treat such infections.

SUMMARY

The synthesis of fluorescent proanthocyanidins (FP) was achieved by the condensation reaction of proanthocyanidins (PAC) with cinnamaldehyde and four cinnamaldehyde derivatives, 4-methylcinnamaldehyde, 4-(dimethylamino) cinnamaldehyde, 4-hydroxy-3,5-dimethoxycinnamaldehyde, and 4-hydroxy-3-methoxycinnamaldehyde. Matrix-assisted laser desorption/ionization time-of-flight mass spectrometry spectra of FP showed masses that correspond to (epi)catechin oligomers attached to at least single, double, or triple moieties of cinnamaldehydes. Synthesized FP exhibited fluorescence at higher excitation and emission wavelengths than PAC and each cinnamaldehyde condensation product exhibited different fluorescent properties. FP were evaluated for their ability to agglutinate extra-intestinal pathogenic *Escherichia coli* (ExPEC). Results indicated that FP were significantly more bioactive (p-value<0.05) for agglutinating ExPEC compared to PAC. Scanning electron microscopy indicated that FP interacts with ExPEC surface structures and suggested that FP have higher affinity with the fimbriae-like structures on the surface of ExPEC in comparison to PAC. In addition, fluorescent microscopy performed on in vitro and in vivo agglutination assays showed that FP were entrapping ExPEC in a web-like network, thus demonstrating agglutination of ExPEC. This study demonstrated the potential of FP to improve our understanding of the temporal and dynamic interactions of PAC in in-vitro and in-vivo studies.

Accordingly, this disclosure provides a fluorescent proanthocyanidin condensation product comprising three or more monomers, wherein each monomer of the three or more monomers is independently selected from the group consisting of Formulas S1, S2, S3, S4, S5 and pyrylium cations thereof:

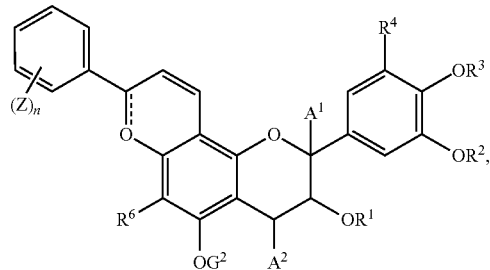

(S1)

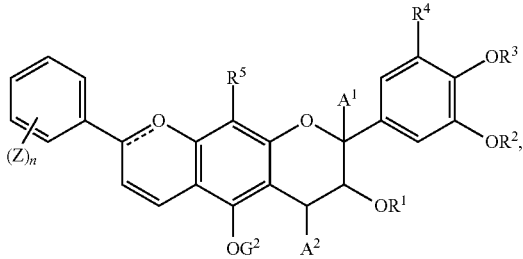

(S2)

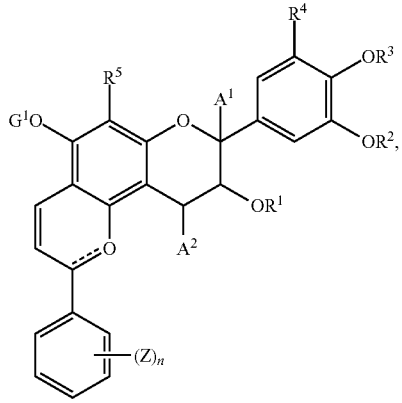

(S3)

-continued

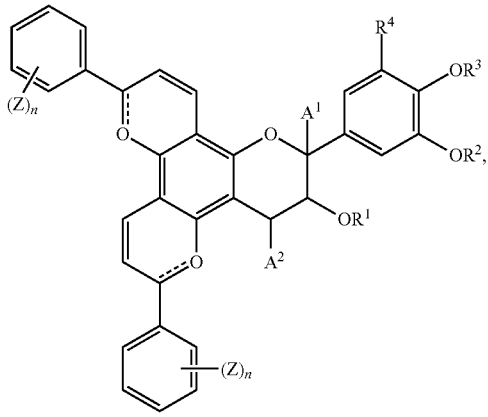

(S4)

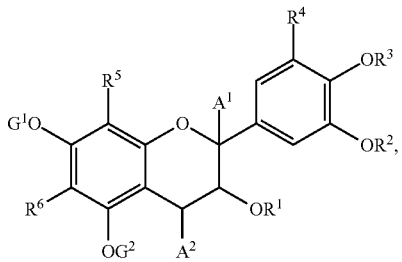

(S5)

wherein

------- represents a single or double bond wherein a pyrylium cation at oxygen (O⁺) is formed when ------- is a double bond;

$A^1$ and $A^2$ are each independently radical or H;

$G^1$ is radical, H, —$(C_1$-$C_6)$alkyl, or —C(=O)$(C_1$-$C_6)$ alkyl;

$G^2$ is H, —$(C_1$-$C_6)$alkyl, or —C(=O)$(C_1$-$C_6)$alkyl;

$R^1$, $R^2$ and $R^3$ are each independently H, —$(C_1$-$C_6)$alkyl, or —C(=O)$(C_1$-$C_6)$alkyl;

$R^4$ is H or $OR^a$ wherein $R^a$ is H, —$(C_1$-$C_6)$alkyl or —C(=O)$(C_1$-$C_6)$alkyl;

$R^5$ and $R^6$ are each independently radical or H;

each Z is independently halo, —$(C_1$-$C_6)$alkyl, $OR^b$, or $N(R^b)_2$, wherein each $R^b$ is independently H, —$(C_1$-$C_6)$alkyl, or —C(=O)$(C_1$-$C_6)$alkyl; and each n is independently 0-5;

wherein an A-type linkage between a first monomer and a second monomer is formed when $A^1$ and $A^2$ of the first monomer are radical, $G^1$ and $R^5$ of the second monomer are radical, $A^1$ and $G^1$ form a bond, and $A^2$ and $R^5$ form a second bond; or a B-type linkage between the first monomer and the second monomer is formed when $A^2$ of the first monomer is radical, $R^5$ or $R^6$ of the second monomer is radical, and $A^2$ and $R^5$ form a bond or $A^2$ and $R^6$ form a bond;

wherein the first monomer is a monomer of Formulas S1 to S4 and the second monomer is a monomer of Formula S2, S3 or S5, and the product is an oligomer having a degree of polymerization of three or more.

Also, this disclosure provides composition comprising the fluorescent proanthocyanidin condensation product shown above and at least one other proanthocyanidin.

Additionally, this disclosure provides a method for forming the fluorescent proanthocyanidin condensation product discussed above, comprising:

a) contacting a naturally occurring proanothocyanidin, 3-phenylprop-2-enal, a metal-salt catalyst, and an acid under suitable reaction conditions for a sufficient amount of time for a condensation reaction to occur; and b) neutralizing the reaction;

thereby forming the product.

Furthermore, this disclosure provides a method for mitigating a bacterial invasion in-vivo or in-vitro comprising:

a) contacting bacteria and a fluorescent proanthocyanidin condensation product as described herein;

b) visualizing and/or quantifying a quantity of agglutinated bacteria by fluorescence microscopy; and c) optionally repeating steps a) and b);

thereby mitigating the bacterial invasion.

The invention provides novel compounds consisting of Formulas I-IV, S1, S2, S3, S4, S5 and pyrylium cations thereof, intermediates for the synthesis of the compounds, as well as methods of preparing the compounds. The invention also provides the compounds that are useful as intermediates for the synthesis of other useful compounds. The invention provides for the use of the compounds for the manufacture of medicaments and diagnosis tools useful for the treatment of bacterial infections in a mammal, such as a human.

The invention provides for the use of the compositions described herein for use in medical examinations and therapy. The medical therapy can be treating bacterial infections, for example, an *E. coli* infection. The invention also provides for the use of a composition as described herein for the manufacture of a medicament to treat a disease in a mammal, for example, an *E. coli* infection in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Proanthocyanidin-cinnamaldehydes pyrylium products (FP) have useful fluorescent properties, i.e., higher excitation and emission wavelength than PAC, for use in microscopy of PAC interactions with bacteria, mammalian cells, and tissues. Although the DMAC assay has been used as a colorimetric method for quantifying PAC content, the existing literature has not described the synthesis of these cinnamaldehyde compounds with PAC for use as fluorophores.

Our research has: (1) characterized the synthesis of FP based on the reactions of PAC with cinnamaldehydes; (2) evaluated the ability of FP to exhibit fluorescence; (3) evaluated the bioactivity of FP to agglutinate extra-intestinal pathogenic *Escherichia coli* (ExPEC) in an in-vitro model; and (4) used fluorescent microscopy to visualize the interactions between FP and ExPEC during in-vitro and in-vivo agglutination. These FP may be used to improve our understanding of the temporal and dynamic interactions of PAC in in-vitro and in-vivo studies. In addition, the use of these FP with fluorescent microscopy is an alternative to complex and expensive techniques such as $^{14}C$ radio-labeling of PAC.

Figure 1:
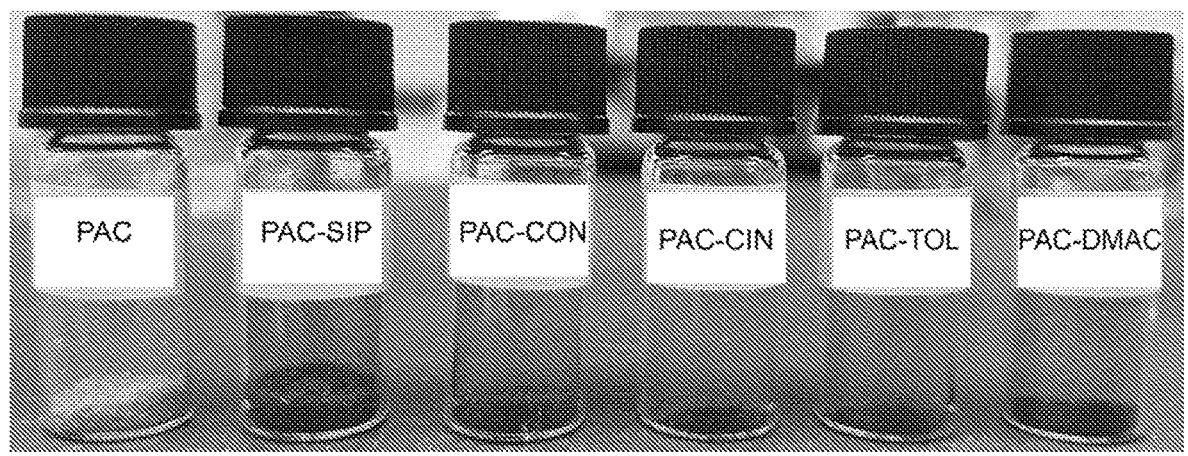
FIG. 1. (A) Illustrative image showing the FP-PAC. (B) Illustrative image showing the fluorescent-labeled pigmented PAC. PAC-DMAC (violet, left) and PAC-CIN (orange, right). Absorbance (C) and Emission (D) spectra for PAC and fluorescent-labeled pigmented PAC (PAC-DMAC and PAC-Cinnamaldehyde).
Figure 1:
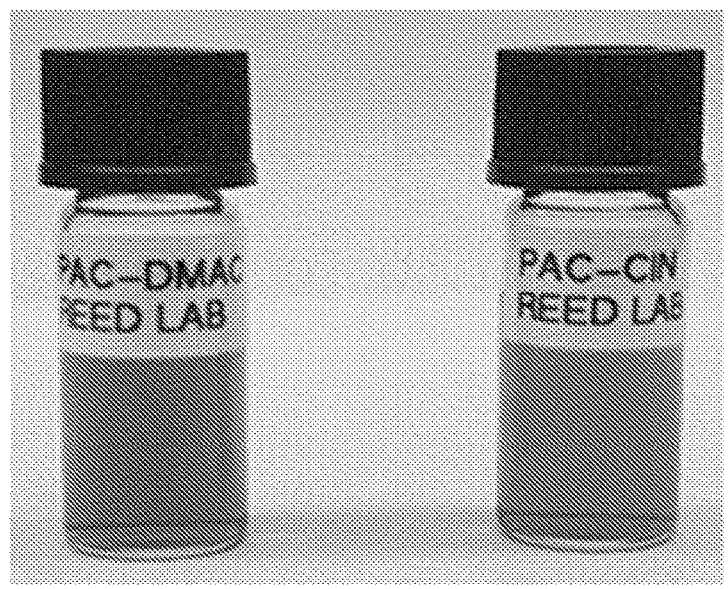
Figure 1:
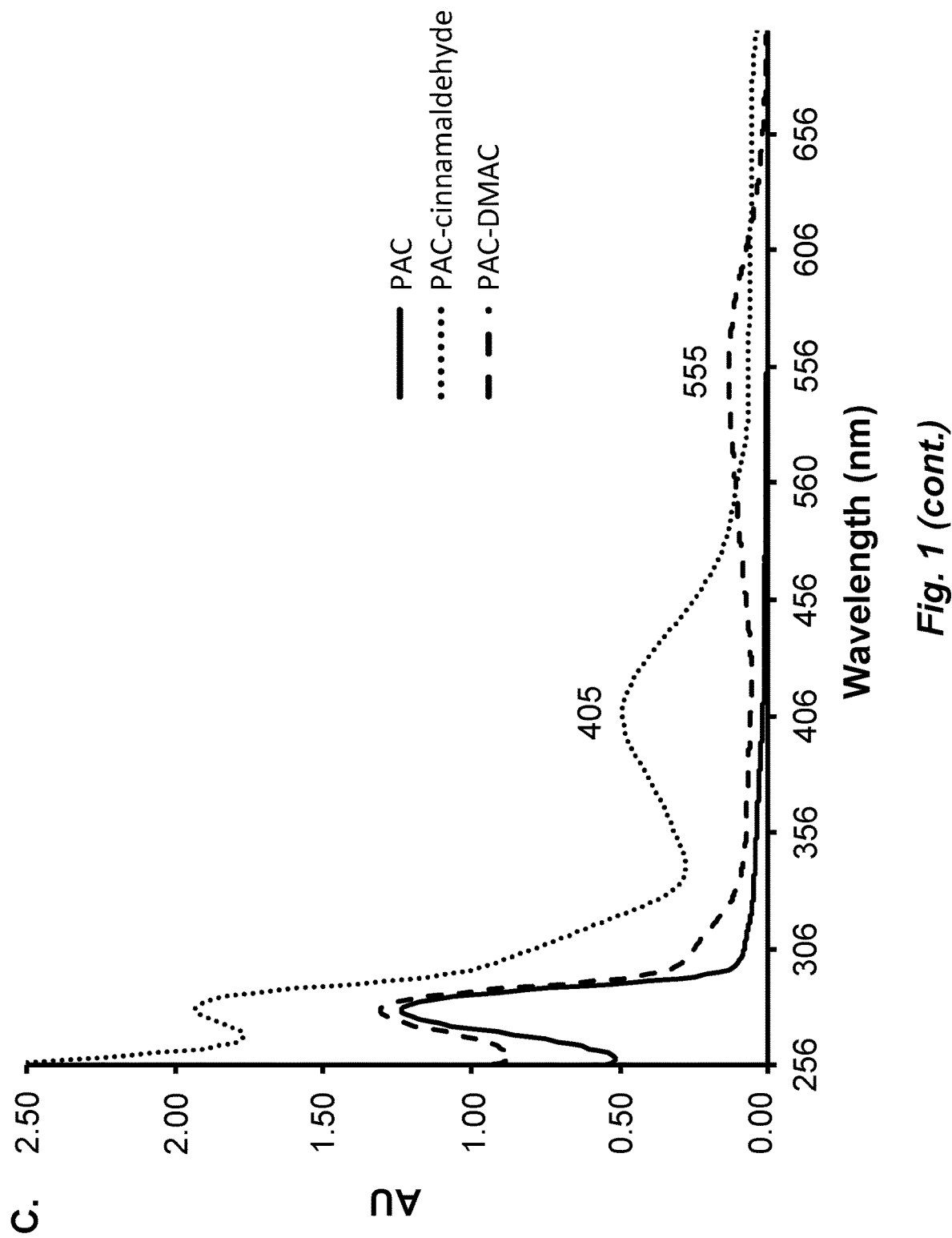
Figure 1:
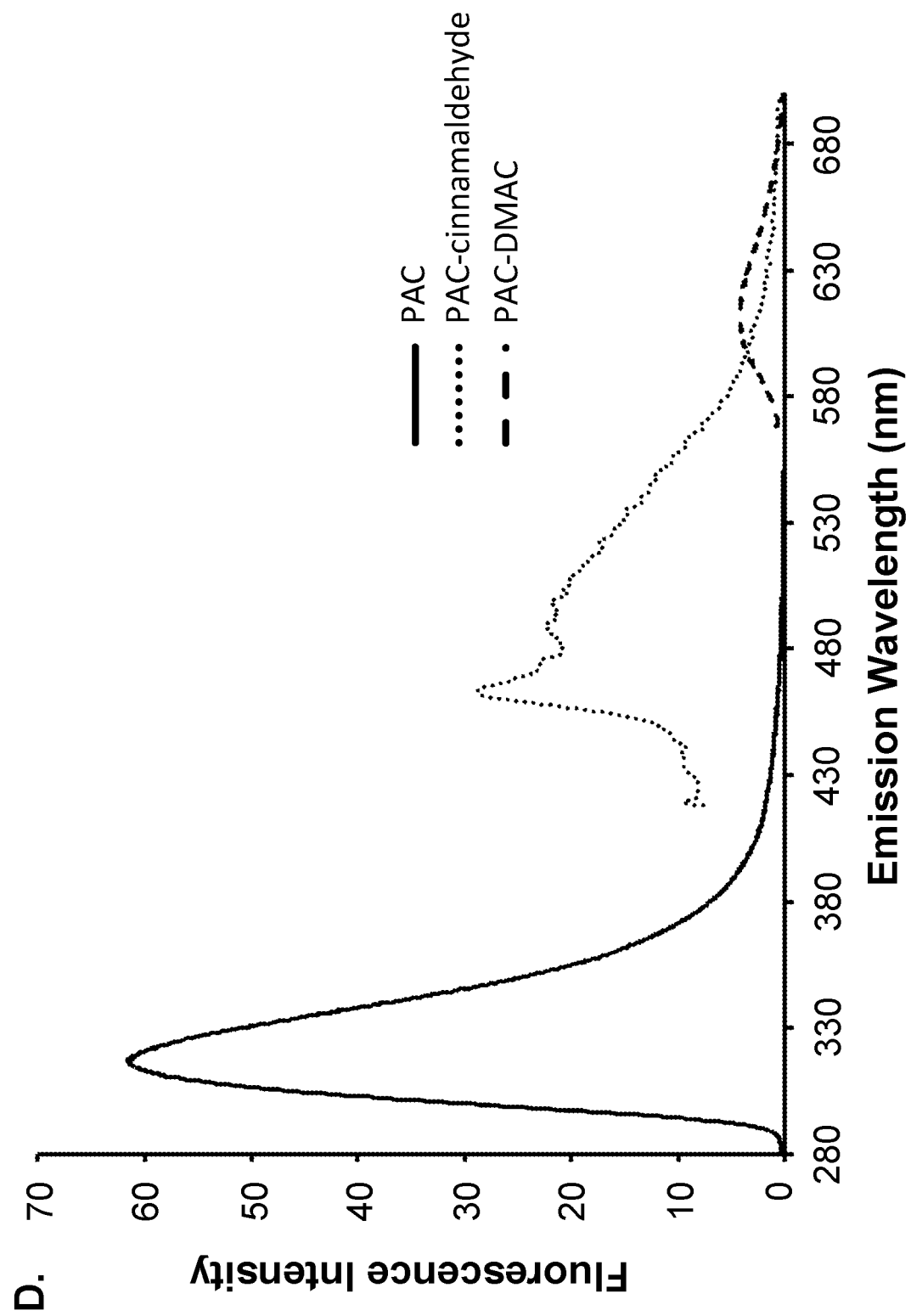

The fluorescent-labeled pigmented PAC maintains the physical-chemical properties of PAC that lead to biomedical applications (FIG. 1). Thus, fluorescent-labeled pigmented PAC can be used to visualize biological processes by fluorescent microscopy. These new fluorescent-labeled pigmented PAC agglutinate (entrapment) *Escherichia coli* (strain CFT073) that expresses green fluorescent protein (GFP) in the same way as PAC alone. The entrapment of *E. coli* was observed by fluorescent microscopy and indicates that the bioactivity of fluorescent-labeled pigmented PAC is the same or perhaps greater than native PAC. Also, we instilled these new fluorescent-labeled pigmented PAC into the bladders of rats in combination with *E. coli* CFT073-GFP. Results indicate that these new fluorescent-labeled pigmented PAC agglutinate *E. coli* CFT073-GFP in the rat bladder, resulting in an entrapment in a web-like network. In addition, the instillation of these new fluorescent-labeled pigmented PAC into the bladders of rats without *E. coli* CFT073-GFP demonstrated agglutination of endogenous bacteria. This finding suggests that these new fluorescent-labeled pigmented PAC have potential as a diagnostic tool for detecting the presence of bacteria in urine.

Additional information and data supporting the invention can be found in the following publication by the inventors: *J. Agric. Food Chem.* 2021, 69, 10700-10708 and its Supporting Information, which are incorporated herein by reference in its entirety.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number 1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

In the context of chemical synthesis, an "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone, or two or more may be mixed, to provide a "solvent system".

The term, "repeat unit", "repeating unit", or "block" as used herein refers to the moiety of a polymer that is repetitive. The repeat unit may comprise one or more repeat units, labeled as, for example, repeat unit A, repeat unit B, repeat unit C, etc. Repeat units A-C, for example, may be covalently bound together to form a combined repeat unit. Monomers or a combination of one or more different monomers can be combined to form a (combined) repeat unit of a polymer or copolymer.

The term "molecular weight" for the copolymers disclosed herein refers to the average number molecular weight ($M_n$). The corresponding weight average molecular weight ($M_w$) can be determined from other disclosed parameters by methods (e.g., by calculation) known to the skilled artisan.

Embodiments of the Invention

This disclosure provides a fluorescent proanthocyanidin condensation product comprising three or more monomers, wherein each monomer unit of the three or more monomers is independently selected from the group consisting of Formulas S1, S2, S3, S4, S5 and pyrylium cations thereof:

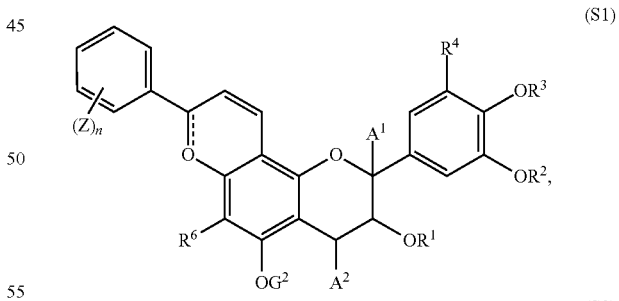

(S1)

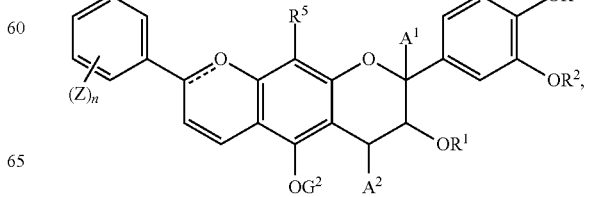

(S2)

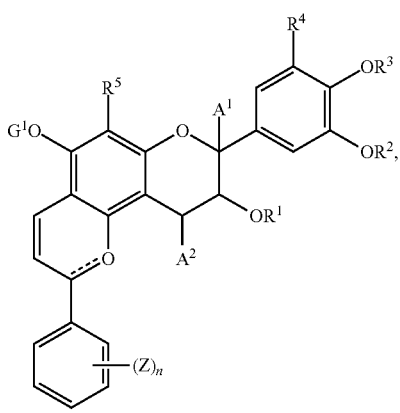

(S3)

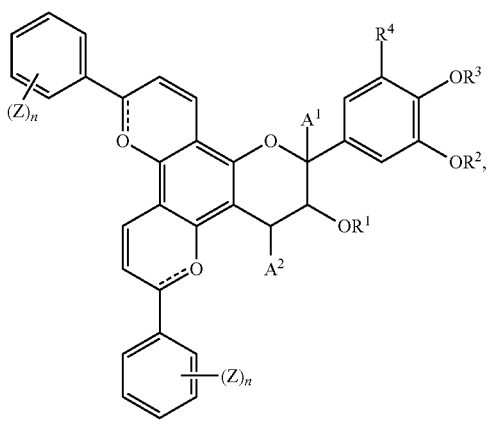

(S4)

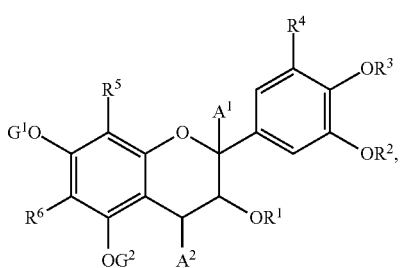

(S5)

wherein

═════ represents a single or double bond wherein a pyrylium cation at oxygen (O$^+$) is formed when ═════ is a double bond;

$A^1$ and $A^2$ are each independently radical or H;

$G^1$ is radical, H, —(C$_1$-C$_6$)alkyl, or —C(═O)(C$_1$-C$_6$)alkyl;

$G^2$ is H, —(C$_1$-C$_6$)alkyl, or —C(═O)(C$_1$-C$_6$)alkyl;

$R^1$, $R^2$ and $R^3$ are each independently H, —(C$_1$-C$_6$)alkyl, or —C(═O)(C$_1$-C$_6$)alkyl;

$R^4$ is H or OR$^a$ wherein R$^a$ is H, —(C$_1$-C$_6$)alkyl or —C(═O)(C$_1$-C$_6$)alkyl;

$R^5$ and $R^6$ are each independently radical or H;

each Z is independently halo, —(C$_1$-C$_6$)alkyl, OR$^b$, or N(R$^b$)$_2$, wherein each R$^b$ is independently H, —(C$_1$-C$_6$)alkyl, or —C(═O)(C$_1$-C$_6$)alkyl; and each n is independently 0-5;

wherein an A-type linkage between a first monomer and a second monomer is formed when $A^1$ and $A^2$ of the first monomer are radical, $G^1$ and $R^5$ of the second monomer are radical, $A^1$ and $G^1$ form a bond, and $A^2$ and $R^5$ form a second bond; or a B-type linkage between the first monomer and the second monomer is formed when $A^2$ of the first monomer is radical, $R^5$ or $R^6$ of the second monomer is radical, and $A^2$ and $R^5$ form a bond or $A^2$ and $R^6$ form a bond.

In various embodiments, the first monomer is a monomer of Formulas S1, S2, S3, S4, or a pyrylium cation thereof. In various embodiments, the second monomer is a monomer of Formula S2, S3, S5 or a pyrylium cation thereof. In various embodiments, the fluorescent proanthocyanidin condensation product is an oligomer having a degree of polymerization (DP) of three or more.

Alternatively, this disclosure provides a fluorescent proanthocyanidin condensation product comprising three or more monomers, wherein one or more monomer units of the three or more monomers is selected from the group consisting of Formulas S1, S2, S3, S4, S5 and pyrylium cations thereof, and the product is an oligomer having a degree of polymerization of three or more, wherein the substituents for Formula S1-S5 are as defined above.

In various embodiments, DP is 3, 4, 5, 6, 7, 8, 9, 10, 11, 12, 13, 14, 15, 16-20, 21-30, 31-40, 41-50, 51-75, 76-100, 100-200, 201-500, 501, or more.

In various embodiments, the product comprises the A-type and/or B-type linkage. In various embodiments, position-4 and position-2 of the first monomer are covalently bonded to position-8 and the oxygen at position-7 of the second monomer, respectively (e.g., 2→7, 4→8 A-type linkage).

In various embodiments, position-4 of the first monomer is covalently bonded to position-8 or position-6 of the second monomer (4→8 B-type linkage or 4→6 B-type linkage).

In various embodiments, the first monomer is a monomer of Formula S1, S2, S3, S4, S5, or a pyrylium cation thereof. In various embodiments, the second monomer is a monomer of Formula S1, S2, S3, S4, S5, or a pyrylium cation thereof. In various embodiments, the third monomer is a monomer of Formula S1, S2, S3, S4, S5, or a pyrylium cation thereof. In various embodiments, a fifth monomer is a monomer of Formula S1, S2, S3, S4, S5, or a pyrylium cation thereof. In various embodiments, a sixth, seventh, eight, ninth, tenth, or additional (n$^{th}$) monomer is a monomer of Formula S1, S2, S3, S4, S5, or a pyrylium cation thereof.

In other embodiments, the product comprises three or more or four or more monomers selected from the group consisting of Formulas S1, S2, S3, S4, S5 and pyrylium cations thereof. In other embodiments, the product comprises five or more monomers selected from the group consisting of Formulas S1, S2, S3, S4, S5 and pyrylium cations thereof. In other embodiments, the product comprises six or more, seven or more, eight or more, nine or more, or ten or more monomers selected from the group consisting of Formulas S1, S2, S3, S4, S5 and pyrylium cations thereof.

In some other embodiments, the fluorescent proanthocyanidin condensation product is a condensation product of cranberry proanthocyanidins or purified cranberry proanthocyanidins. In other embodiments, the fluorescent proanthocyanidin condensation product has an overall degree of polymerization of two or more, three or more, four or more, five or more, six or more, seven or more, eight or more, nine or more, or ten or more.

In some embodiments, the product has the A-type linkage between the first monomer and the second monomer. In other embodiments, the product has the B-type linkage between the first monomer and the second monomer. In yet other embodiments, the product has the A-type linkage between the second monomer and a third monomer wherein the third monomer is a monomer of Formula S2, S3 or S5. In some other embodiments, the second monomer is a monomer of Formula S5.

In some embodiments, the linkage is a B-type linkage. In some embodiments, the B-type linkage is to a monomer of Formula S5 at the 6-position or the 8-position. In some embodiments, the radical $A^2$ of the first monomer and the radical $R^5$ or radical $R^6$ of the second monomer form a B-type linkage.

In various embodiments, $R^4$ is H. In various embodiments, $R^1$, $R^2$ and $R^3$ are H. In other embodiments, $G^1$ is radical or H and $G^2$ is H. In various embodiments, n is 1-3. In various embodiments, the product comprises a pyrylium cation. In various embodiments, each Z is independently $CH_3$, OH, $OCH_3$, or $N(CH_3)_2$. In various embodiments, each phenyl moiety substituted by $(Z)_n$ in Formulas S1 to S4 is independently:

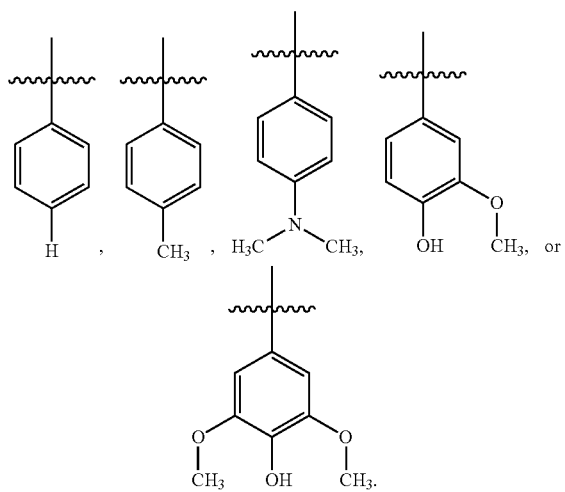

In various additional embodiments, the product is an oligomer where the first three monomers, $n^{th}$ monomer, first two linkages, and $n^{th}-1$ linkage in the oligomer are represented by the general formula (X): $M-L-M-L-M-L_{n-1}-M_n$- (X), wherein M is selected from the group consisting of Formulas S1, S2, S3, S4, S5 and pyrylium cations thereof (shown above); L is an A-type linkage or B-type linkage; and n is 10,000 or less.

In some embodiments, the general formula (X) represents oligomers having 20 monomers or less, 30 monomers or less, 40 monomers or less, 50 monomers or less, 100 monomers or less, or 1000 monomers or less. Examples of oligomers are shown, but not limited to the entries, in Table 1.

TABLE 1

Examples showing the first three monomers of the oligomeric fluorescent proanthocyanidin condensation product**.

| No. | $M_1$ | $L_1$ | $M_2$ | $L_2$ | $M_3$ | No. | $M_1$ | $L_1$ | $M_2$ | $L_2$ | $M_3$ |
|---|---|---|---|---|---|---|---|---|---|---|---|
| 1 | S1 | A | S5 | A | S5 | 2 | S1 | B | S5(6) | B | S5 |
| 3 | S1 | B | S5 | B | S5 | 4 | S1 | B | S5 | B | S5(6) |
| 5 | S1 | A | S5 | B | S5 | 6 | S1 | A | S5 | B | S5(6) |
| 7 | S1 | B | S5 | A | S5 | 8 | S1 | B | S5(6) | A | S5 |
| 9 | S2 | A | S5 | A | S5 | 10 | S2 | B | S5(6) | B | S5 |

TABLE 1-continued

Examples showing the first three monomers of the oligomeric fluorescent proanthocyanidin condensation product**.

| No. | $M_1$ | $L_1$ | $M_2$ | $L_2$ | $M_3$ | No. | $M_1$ | $L_1$ | $M_2$ | $L_2$ | $M_3$ |
|---|---|---|---|---|---|---|---|---|---|---|---|
| 11 | S2 | B | S5 | B | S5 | 12 | S2 | B | S5 | B | S5(6) |
| 13 | S2 | A | S5 | B | S5 | 14 | S2 | A | S5 | B | S5(6) |
| 15 | S2 | B | S5 | A | S5 | 16 | S2 | B | S5(6) | A | S5 |
| 17 | S3 | A | S5 | A | S5 | 18 | S3 | B | S5(6) | B | S5 |
| 19 | S3 | B | S5 | B | S5 | 20 | S3 | B | S5 | B | S5(6) |
| 21 | S3 | A | S5 | B | S5 | 22 | S3 | A | S5 | B | S5(6) |
| 23 | S3 | B | S5 | A | S5 | 24 | S3 | B | S5(6) | A | S5 |
| 25 | S4 | A | S5 | A | S5 | 26 | S4 | B | S5(6) | B | S5 |
| 27 | S4 | B | S5 | B | S5 | 28 | S4 | B | S5 | B | S5(6) |
| 29 | S4 | A | S5 | B | S5 | 30 | S4 | A | S5 | B | S5(6) |
| 31 | S4 | B | S5 | A | S5 | 32 | S4 | B | S5(6) | A | S5 |

**When the linkage (L) is B-type and the next monomer (M) is S5, the bond is at the 8-position of S5.

When the bond is at the 6-position of S5, then S5 is represented as S5(6). Position numbering of Formula S5 is shown as:

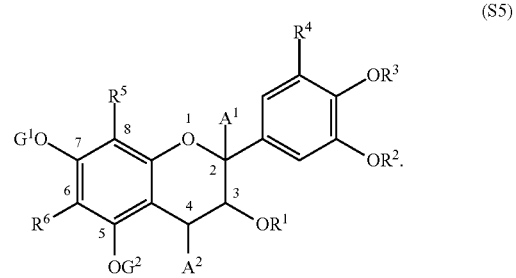

(S5)

In additional embodiments, the product comprises any one of Formulas I-IV:

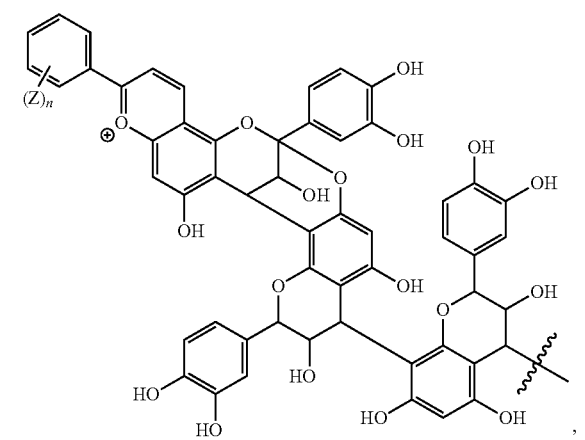

(I)

-continued (II)

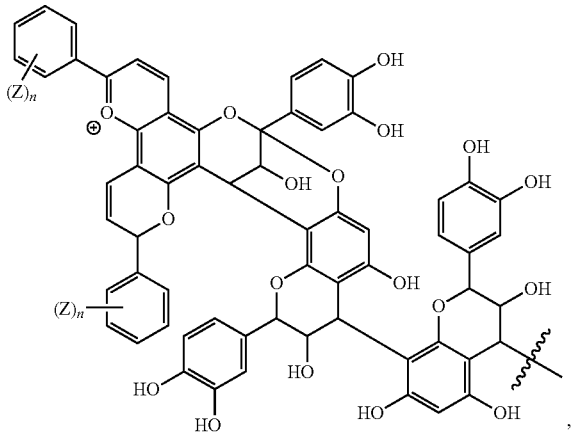

(III)

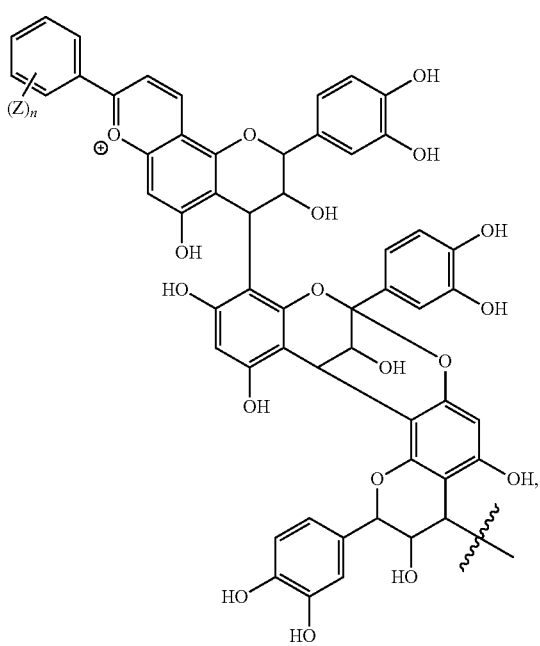

-continued (IV)

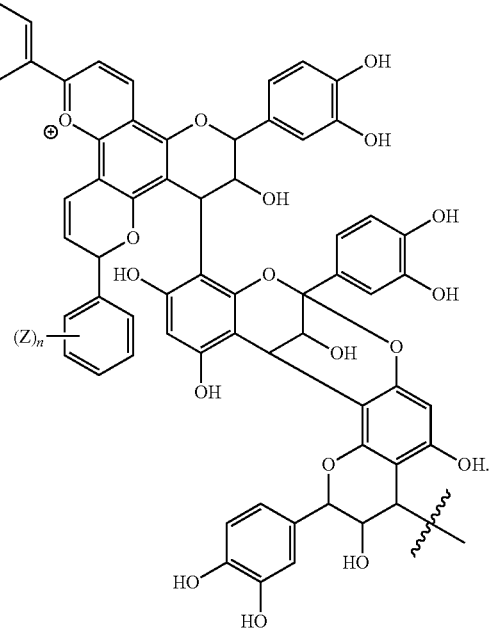

In some embodiments, Z is $N(R^b)_2$. In some embodiments, Z is in the para-position or 4-position. In some embodiments, $R^b$ is $CH_3$. In some embodiments, n is 1. In some embodiments, at least one Z is in the para-position (e.g., 4-position), wherein Z is $N(CH_3)_2$ and n is 1.

In various embodiments, the product has an absorption maximum wavelength of about 350 nanometers to about 600 nanometers. In various embodiments, the product has an emission maximum wavelength of about 450 nanometers to about 650 nanometers. In various embodiments, the product is capable of fluorescence.

Also, this disclosure provides a composition comprising the fluorescent proanthocyanidin condensation product disclosed herein and at least one other proanthocyanidin.

Additionally, this disclosure provides a method for forming the fluorescent proanthocyanidin condensation product described herein comprising:
  a) contacting a naturally occurring proanothocyanidin, 3-phenylprop-2-enal, a metal-salt catalyst, and an acid under suitable reaction conditions for a sufficient amount of time for a condensation reaction to occur; and
  b) neutralizing the reaction;
thereby forming the product.

In various embodiments, the naturally occurring proanothocyanidin is obtained or isolated from cranberries. In various embodiments, the metal-salt catalyst is a magnesium salt, magnesium chloride, magnesium sulfate, a magnesium salt, a copper salt, or an iron salt. In other embodiments, the acid is hydrochloric acid.

In various embodiments, the hydrochloric acid is about 0.05 M to about 2 M hydrochloric acid. In other embodiments, the hydrochloric acid is about 0.2 M, about 0.3 M, or about 0.4 M hydrochloric acid. In other embodiments, the contacting comprises a solvent. In other embodiments, the solvent is an alcohol such as methanol or ethanol.

In various embodiments, the pH of the reaction mixture is about: 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, or 7-14.

Also, this disclosure provides a method for quantifying and mitigating bacterial infections by agglutinating the bacteria and preventing bacterial invasion of epithelial cells in-vivo or in-vitro comprising:
a) contacting bacteria and the fluorescent proanthocyanidin condensation product described herein;
b) visualizing and/or quantifying a quantity of agglutinated bacteria by fluorescence microscopy; and/or
c) optionally repeating steps a) and b);
thereby mitigating bacterial infections by agglutinating the bacteria and preventing bacterial invasion of epithelial cells.

This disclosure also provides a method for quantifying the presence of bacteria in-vivo or in-vitro comprising:
a) contacting bacteria in a subject or sample and a fluorescent proanthocyanidin condensation product described herein;
b) contacting bacteria in a control subject or control sample and the fluorescent proanthocyanidin condensation product described herein;
c) comparing fluorescence intensity of agglutinated bacteria in the subject and control subject or the sample and control sample; and
d) quantifying the agglutinated bacteria in the subject or sample;
thereby quantifying bacteria in-vivo or in-vitro.

In various embodiments, the bacteria is *Escherichia coli*. In various embodiments, a fluorescent proanthocyanidin condensation product described herein selectively agglutinates a bacteria or the *Escherichia coli*.

In various embodiments, the agglutinated bacteria is visualized by fluorescence microscopy. In various embodiments, fluorescence of a proanthocyanidin condensation product or fluorescence of a subject or sample that is agglutinated by the proanthocyanidin condensation product is induced, for example, with electromagnetic radiation of a suitable wavelength. In various embodiments, a bacterial infection is present in the mucosa of a urogenital tract, or is present in the mucosa of a gastrointestinal tract.

Additionally, this disclosure provides a method for treating a bacterial infection in a subject in need thereof, comprising administering an effective amount or effective concentration of the fluorescent proanthocyanidin condensation product disclosed herein to the subject, thereby treating the bacterial infection. In some embodiments, the bacterial infection is an *Escherichia coli* bacterial infection.

Results and Discussion

Synthesis and characterization of proanthocyanidin-cinnamaldehydes pyrylium products. Similar to the known mechanism to explain the formation of catechin-pyrylium and procyanidin-pyrylium products, we found that PAC react with cinnamaldehydes in acidic conditions to form FP, which in turn produce fluorescence. Scheme 1 shows the hypothetical structures of single and double cinnamaldehyde moieties of FP trimers resulting from the reaction between PAC and CIN.

The synthesis of FP produced a dark-amber color for PAC-CIN, a light-amber color for PAC-TOL, a purple color for PAC-DMAC, a red color for PAC-CON, and a red-brick color for PAC-SIN. Based on the ratio of weight of the isolated FP to the sum of the reactants (PAC and cinnamaldehydes). The yield obtained for PAC-CIN was 69% (w/w), 80% (w/w) for PAC-TOL, 64% (w/w) for PAC-DMAC, 75% (w/w) for PAC-CON, and 76% (w/w) for PAC-SIN.

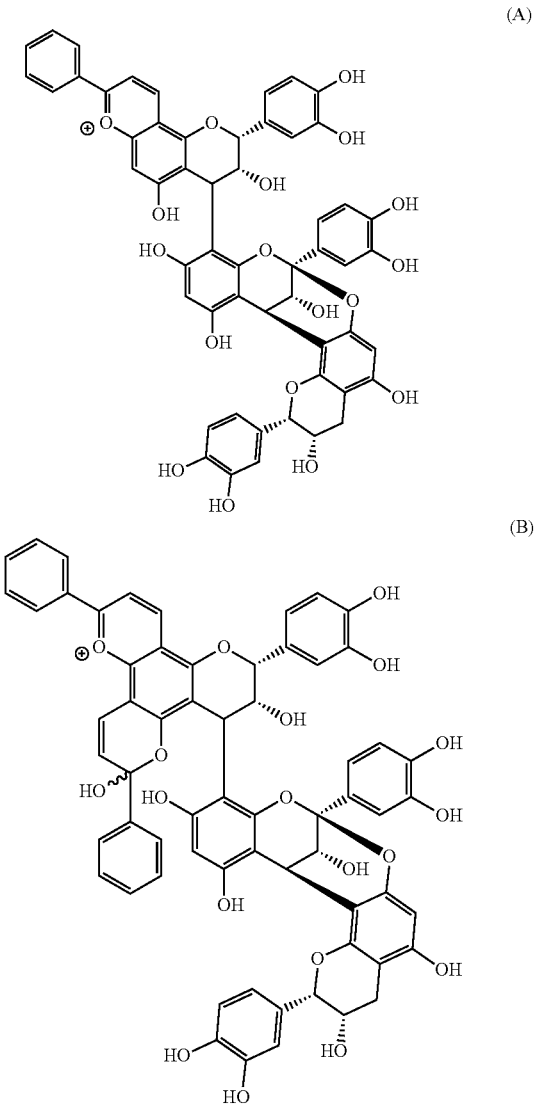

Scheme 1. Hypothetical structures of proanthocyanidin trimers with one A-type interflavan bond covalently linked to a singe (A) and double (B) cinnamaldehyde moieties.

Figure 2:
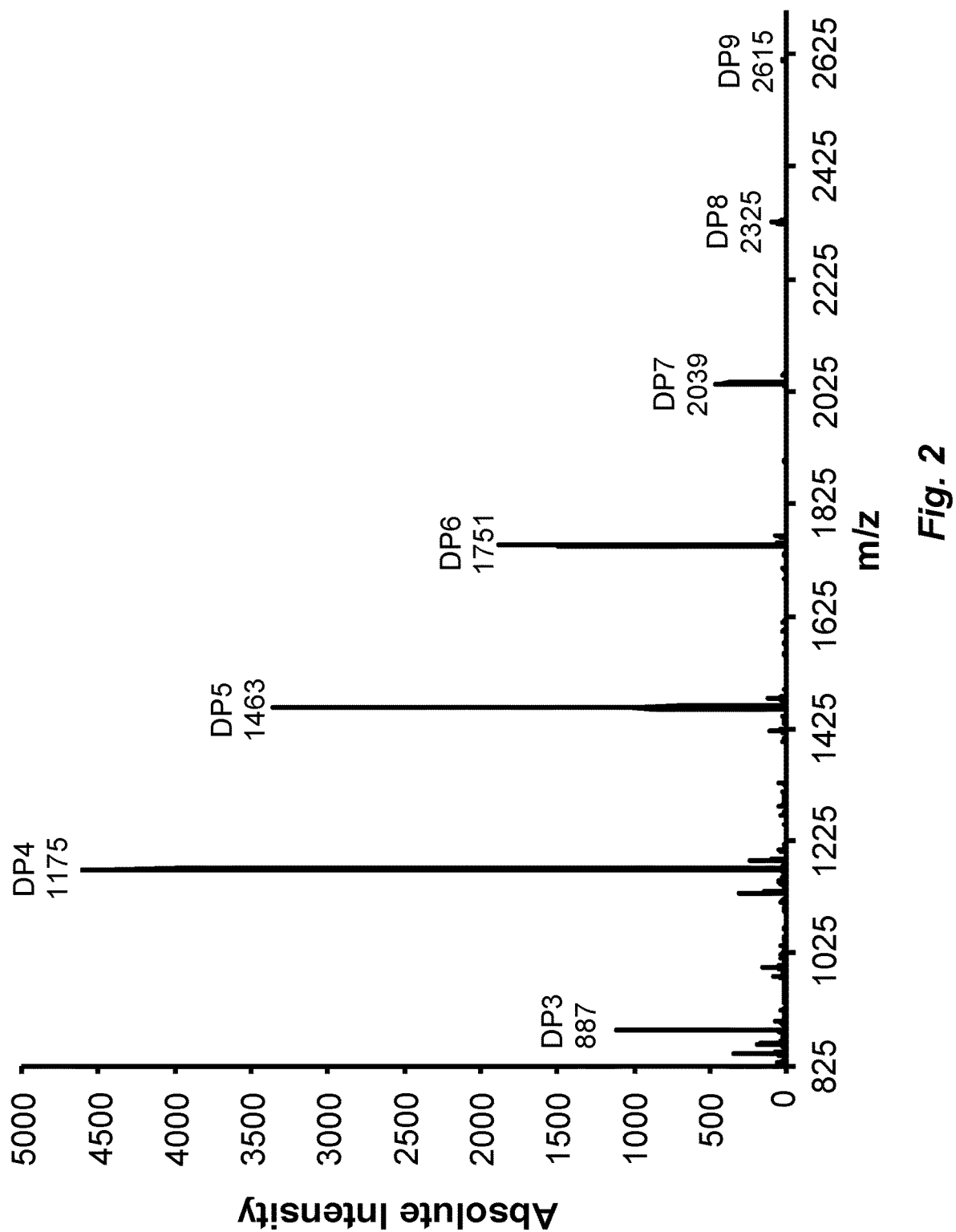
FIG. 2. MALDI-TOF MS spectra in positive reflectron mode for PAC, which show PAC oligomers from trimers to nonamers detected as sodium adducts [M+Na]⁺.
Figure 3:
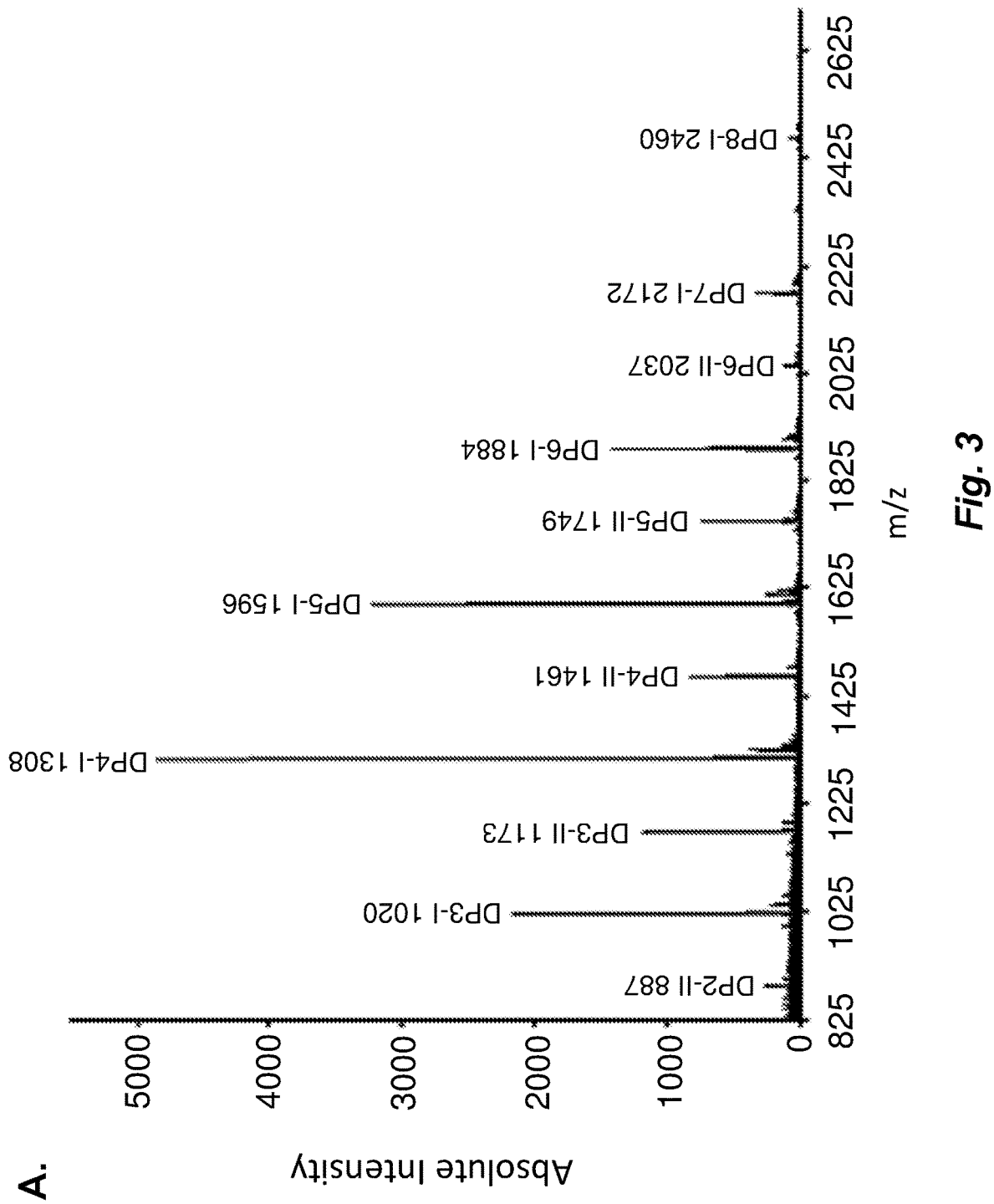
FIG. 3. (A) MALDI-TOF MS spectra in positive reflectron mode for PAC-DMAC, which show PAC oligomers from trimers to octamers. Roman numerals followed by the DP represent the numbers of DMAC moieties attached. (B) MALDI-TOF MS spectra in positive reflectron mode for PAC-CIN, which show PAC oligomers from trimers to hexamers. Roman numerals followed by the DP represent the numbers of CIN moieties attached. (C) MALDI-TOF MS spectra in positive reflectron mode for PAC-TOL, which show PAC oligomers from trimers to octamers. Roman numerals followed by the DP represent the numbers of TOL moieties attached. (D) MALDI-TOF MS spectra in positive reflectron mode for PAC-CON, which show PAC oligomers from trimers to octamers. Roman numerals followed by the DP represent the numbers of CON moieties attached. (E) MALDI-TOF MS spectra in positive reflectron mode for PAC-SIN, which show PAC oligomers from trimers to octamers. Roman numerals followed by the DP represent the numbers of SIN moieties attached.
Figure 3:
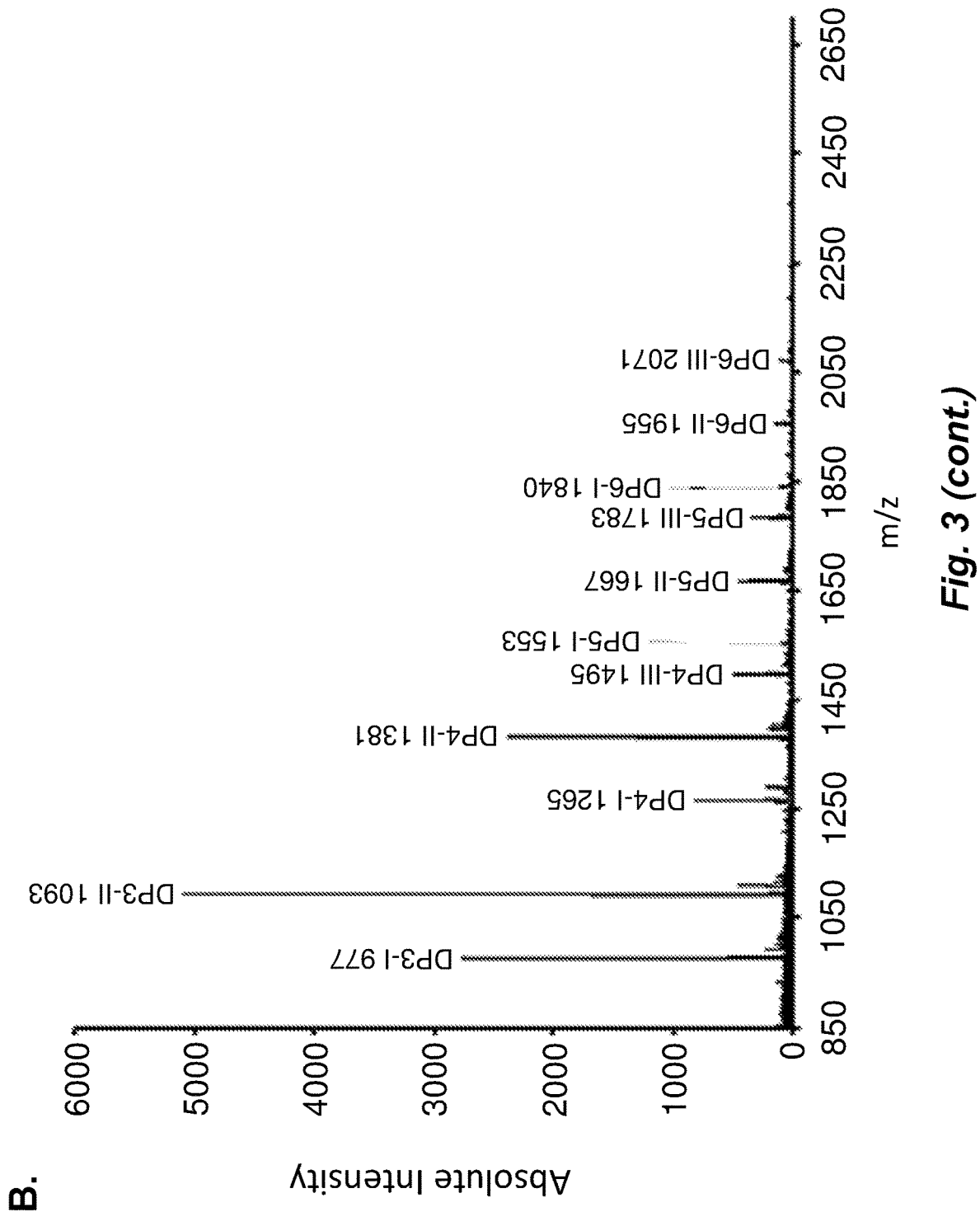
Figure 3:
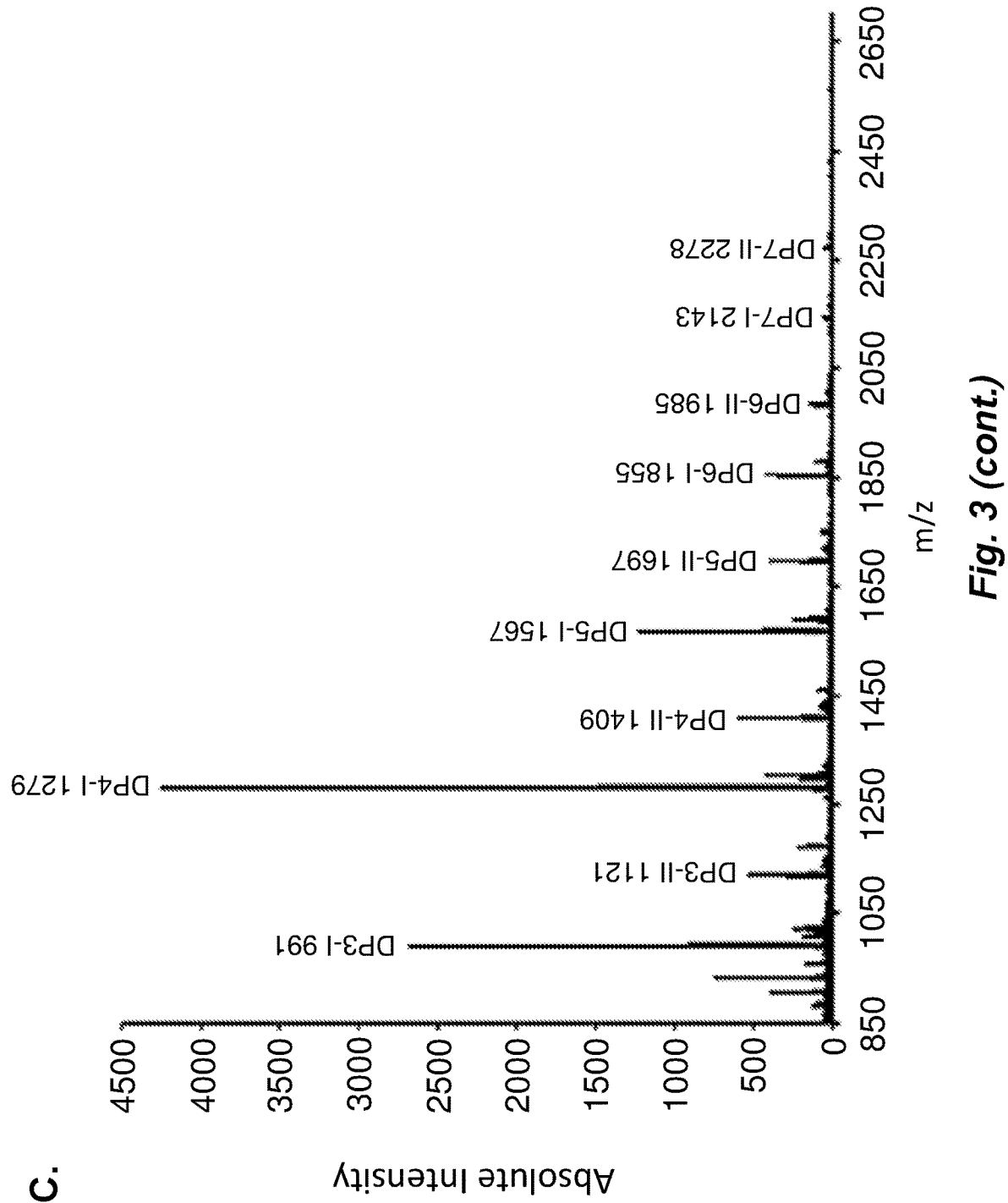
Figure 3:
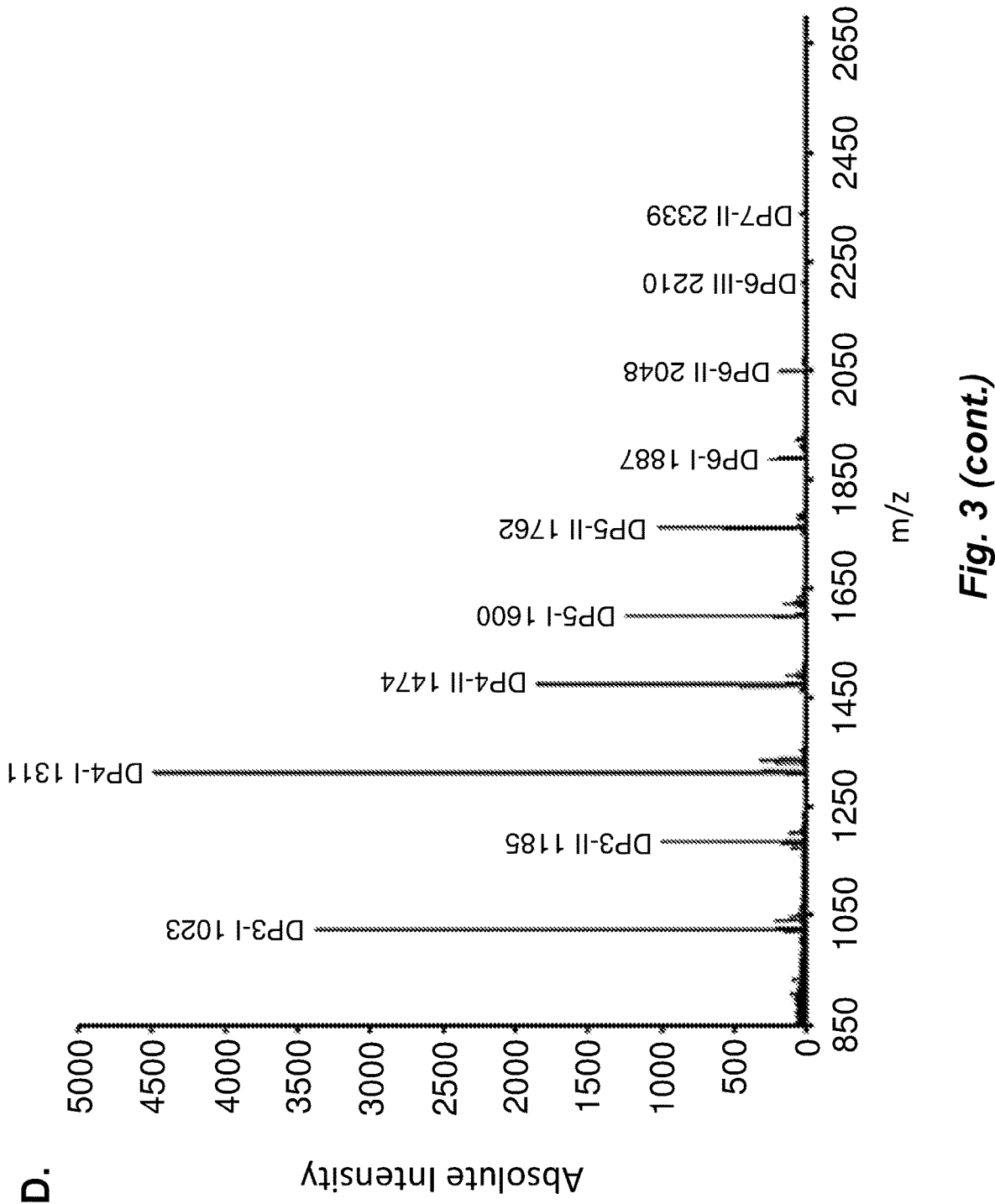
Figure 3:
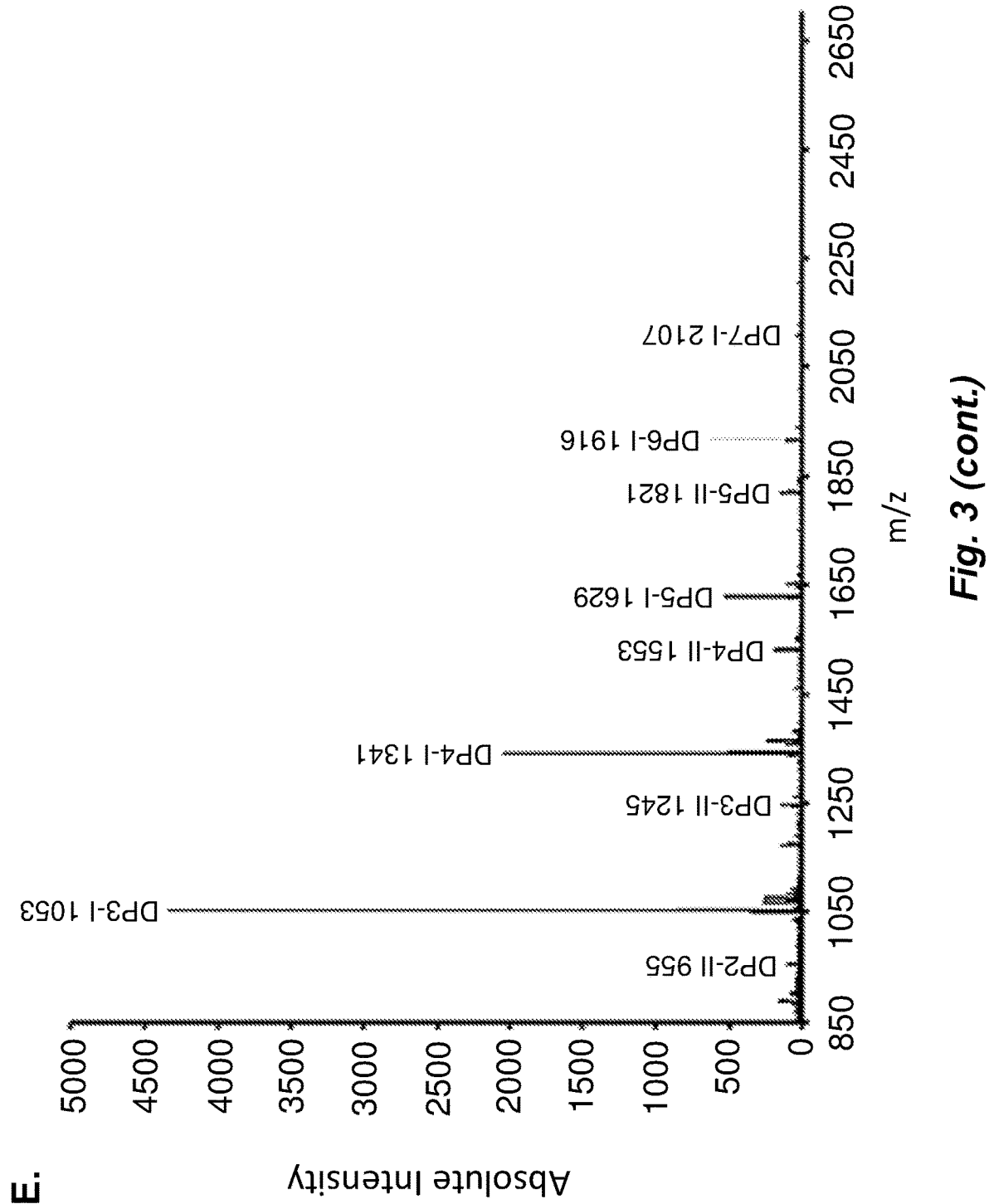

MALDI-TOF MS spectra were used to characterize PAC extracted from cranberry, FP, and non-charged conjugates of FP. The MALDI-TOF MS spectrum of PAC detected oligomeric (epi)catechin units in positive reflectron mode from trimers to nonamers with structural variation in the nature of the interflavan bonds (A- and B-type) (FIG. 2). The isotope patterns of MALDI-TOF MS for the oligomeric (epi)catechin units revealed that masses corresponding to PAC with one A-type interflavan bond had the highest intensity. The masses of oligomeric (epi)catechin units are predicted by the equation m/z=290+288d−2A+b, where 290 represents the molecular weight of the terminal (epi)catechin unit, d is the number of (epi)catechin extension units, A is the number of A-type interflavan linkages, and b is the atomic weight of sodium cations (23 Da) (J. of Agricultural and Food Chemistry, 2003, 51(3), 538).

The MALDI-TOF MS spectra of FP show masses that correspond to (epi)catechin oligomers attached to one, two, or three DMAC (FIG. 3A), CIN, TOL, CON, or SIN moieties (FIG. 3B-3E). The isotope patterns of MALDI-TOF MS for FP with single CIN, TOL, DMAC, CON, or SIN moieties revealed that FP with one A-type interflavan bond had the highest intensity. FP masses detected as pyrylium ions [M]$^+$ with single CIN, TOL, DMAC, CON, or SIN moieties are predicted by the equation m/z=290+288d−2A+X−H$_2$O−H, where 290 represents the molecular weight of the terminal (epi)catechin unit, d is the number of (epi)catechin extension units, A is the number of A-type interflavan bonds, X represent the molecular weight of the cinnamaldehydes [(CIN=132 Da), (TOL=146 Da), (DMAC=175 Da), (CON=178 Da), and (SIN=208 Da)], H$_2$O represents the molecular weight of water (18 Da), and H is the hydrogen atom (1 Da). H$_2$O and H are lost during the condensation reaction.

The isotope patterns of MALDI-TOF MS for FP with two or three CIN, TOL, DMAC, CON, or SIN moieties revealed that FP with zero or two A-type interflavan bonds had the highest intensity. FP masses detected as pyrylium ions with two or three CIN, TOL, DMAC, CON, or SIN moieties with zero A-type interflavan bonds are predicted by the equation m/z=290+288d+nX−nH$_2$O−H, whereas with two A-type interflavan bonds are predicted by the equation m/z=290+288d−2A+nX−nH$_2$O−H, where 290 represents the molecular weight of the terminal (epi)catechin unit, d is the number of (epi)catechin extension units, A is the number of A-type interflavan bonds, n is the number of cinnamaldehydes moieties, X represent the molecular weight of the cinnamaldehydes [(CIN=132 Da), (TOL=146 Da), (DMAC=175 Da), (CON=178 Da), and (SIN=208 Da)], H$_2$O represent the molecular weight of water (18 Da), and H is the hydrogen atom (1 Da) lost during the condensation reaction. In addition, signals with mass differences of 23 Da higher to FP with one, two or three CIN, TOL, DMAC, CON, or SIN moieties were observed. Usually, in MALDI-TOF MS, mass differences of 23 Da correspond to sodium adducts. Thus, signals with mass differences of 23 Da higher to FP with CIN, TOL, DMAC, CON, or SIN moieties correspond to non-charged conjugates of FP, which are detected as sodium adducts. FIG. 3A, FIG. 3C-3E and FIG. 6 show that the relative intensity of non-charged conjugates of FP was below 10%, which suggests that FP detected as pyrylium ions are predominant. The cation in the FP can resonate over the FP molecules, resulting in highly delocalized systems. These delocalized systems are often responsible for absorbing light in the visible region and producing colored compounds.

Ability of proanthocyanidin-cinnamaldehydes pyrylium products to exhibit fluorescence. The UV/Vis spectrum of PAC revealed one $\lambda_{max}$ at 280 nm, whereas the UV/Vis spectra of FP revealed two absorption bands. The first $\lambda_{max}$ was at 280 nm that corresponds to PAC, while the second $\lambda_{max}$ of the FP were at higher wavelengths that differed among the cinnamaldehyde substitutions. The second $\lambda_{max}$ absorption was at 404 nm for PAC-CIN, 416 nm for PAC-TOL, 559 nm for PAC-DMAC, 443 nm for PAC-CON, and 460 nm for PAC-SIN (Table 2, FIG. 1C and FIG. 1D). Previous studies indicate that the addition of electron-donating functional groups, which increases the electron density of the π system via resonance- or inductive-donating effects, alters absorption and emission spectra. Thus, differences in the second $\lambda_{max}$ absorptions, which result from the pyrylium substitutions could be explained by the ability of the functional groups of the cinnamaldehydes to contribute to the resonance structures of the conjugated system, driven by alkyl, methoxy, hydroxy, and tertiary amine groups.

TABLE 2

Absorption and emission maximum wavelengths with their respective stoke shifts for PAC and FP-PAC.

|  | $\lambda_{max}$ absorption | $\lambda_{max}$ emission | Stoke shifts |
| --- | --- | --- | --- |
| PAC | 280 | 320 | 40 |
| PAC-CIN | 404 | 473 | 69 |
| PAC-TOL | 416 | 480 | 64 |
| PAC-DMAC | 559 | 613 | 54 |
| PAC-CON | 443 | 524 | 81 |
| PAC-SIP | 460 | 536 | 76 |

First, alkyl and methoxy groups differ in the electron density that each one donates to the conjugate π system via resonance- or inductive-donating effects. Alkyl groups are located in the inductive-donating effect, whereas the methoxy groups are located in the resonance-donating effect. The resonance-donating effect has lower ionization potential than the induction-donating effect. Second, both methoxy and hydroxy groups are located in the resonance-donating effect. However, the lone pair of electrons in the methoxy group is disturbed by hyperconjugation of the antibonding molecular orbital of the C—H bonds. This effect is absent in the hydroxy group. Third, both hydroxy and tertiary amine groups are located in the resonance-donating effect. However, the lower electronegativity of the N atom compared to the O atom makes the tertiary amine a better electron-donating group.

The fluorescence spectra of PAC and FP revealed $\lambda_{max}$ emission for PAC at 320 nm, 473 nm for PAC-CIN, 480 nm for PAC-TOL, 613 nm for PAC-DMAC, 524 nm for PAC-CON, and 536 nm for PAC-SIN. The Stoke shifts value found for PAC was 40 nm, 69 nm for PAC-CIN, 64 nm for PAC-TOL, 54 nm for PAC-DMAC, 81 nm for PAC-CON, and 76 nm for PAC-SIN. The Stoke shifts are indicative of a change from the excited state to the ground state, which according to the Jablonski diagram, indicates strong excitation light separate from the weak emitted fluorescence. Results indicate that each of the five FP exhibits unique and useful excitation and emission wavelengths. These characteristics demonstrate that FP are a new class of fluorescent probes. For instance, by complexing FP with proteins, glycoproteins, or polysaccharides the visualization of each complex by fluorescent microscopy may be achieved. However, because the fluorescence of FP may be affected by temperature, pH, metals ions, and solvent polarity/viscosity, future work with FP should evaluate the effect of intensity and fluorescence lifetime. For instance, previous studies indicate that the fluorescence intensity of rhodamine-B is temperature-dependent and that the fluorescence lifetime decrease as the polarity of the solvent increases.

Figure 4:
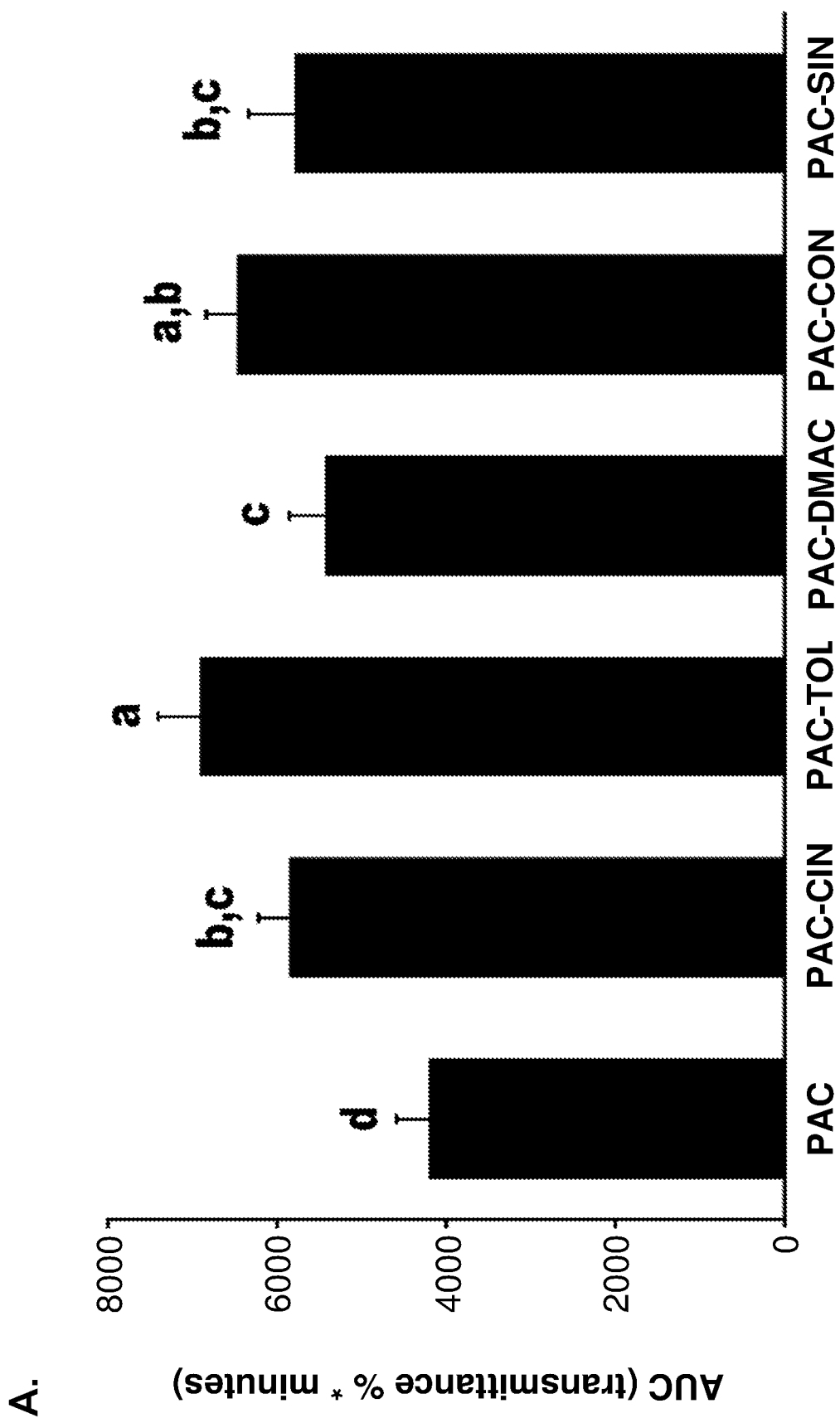
FIG. 4. (A) Area under the curve (AUC) obtained for the agglutination assay with ExPEC in PBS 1× ($Ca^{2+}/Mg^{2+}$) at a fixed concentration of 200 μg/mL of PAC equivalent for PAC and FP. The results represent the average of five independent replicates±standard deviation. Different letters correspond to significant differences at p-value<0.05. (B) Relationship between transmittance (%) at 450 nm and time over 240 min of the agglutination assay with *E. coli* CFT073-GFP for PAC alone and PAC-DMAC at 100 μg/mL of PAC equivalent.
Figure 4:
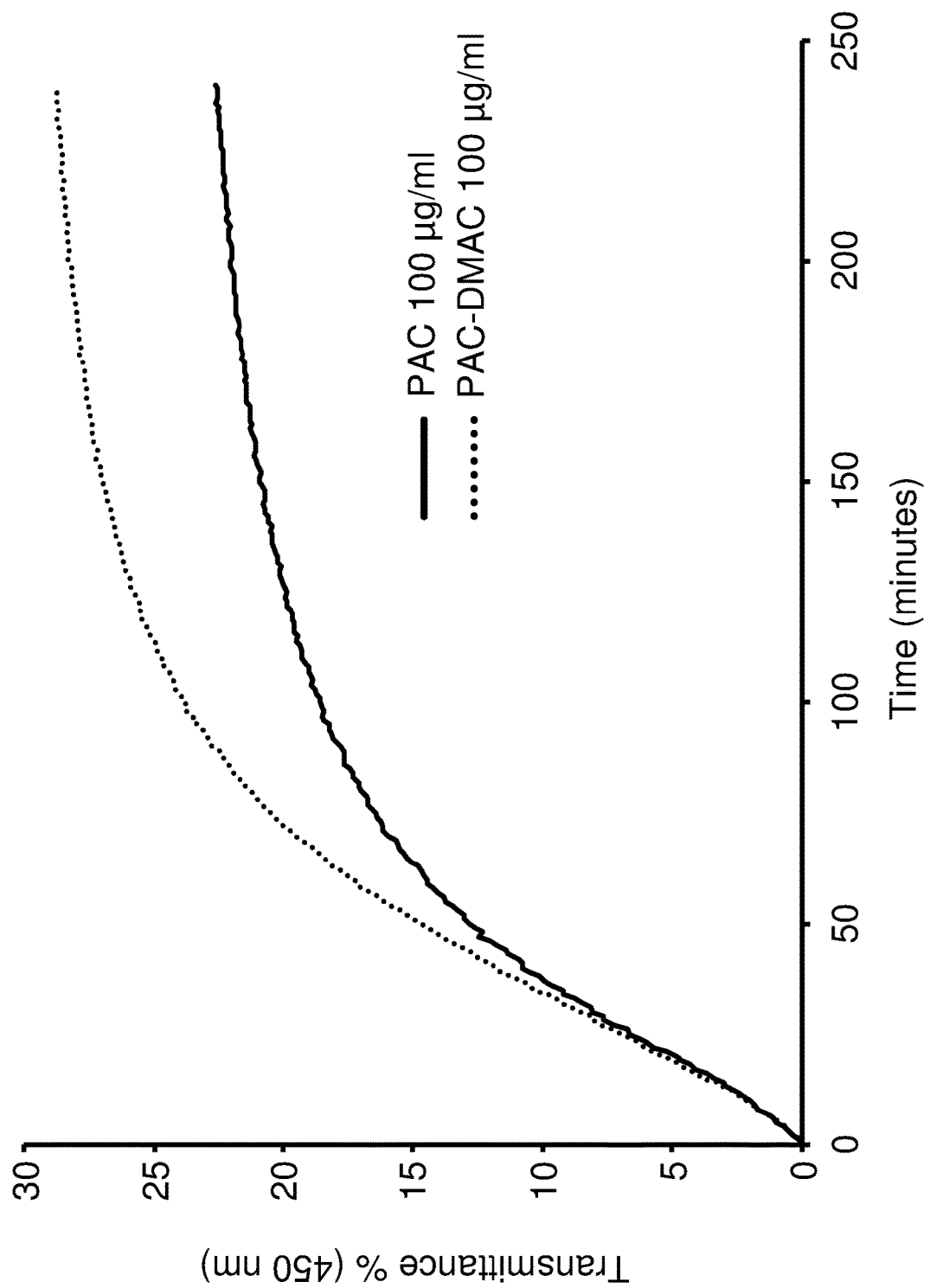

Bioactivity of proanthocyanidin-cinnamaldehyde pyrylium products to agglutinate extra-intestinal pathogenic *Escherichia coli*. PAC and FP were compared for their ability to agglutinate ExPEC (FIG. 4A). Results of the agglutination assay indicate that, at a fixed concentration of 200 μg/mL of PAC equivalent, PAC and FP have the ability to agglutinate ExPEC. As the bacteria agglutinate and precipitate from suspension, an increase in transmittance (600 nm) occurs (also see FIG. 4B). Results suggest that FP were significantly more bioactive (p-value<0.05) for agglutinating ExPEC compared to PAC at a fixed concentration of 200 μg/mL of PAC equivalent. These results suggest that the cinnamaldehydes attached to PAC were not detrimental to PAC agglutination activity. In addition, cinnamaldehydes (negative controls) showed no agglutination.

Figure 5:
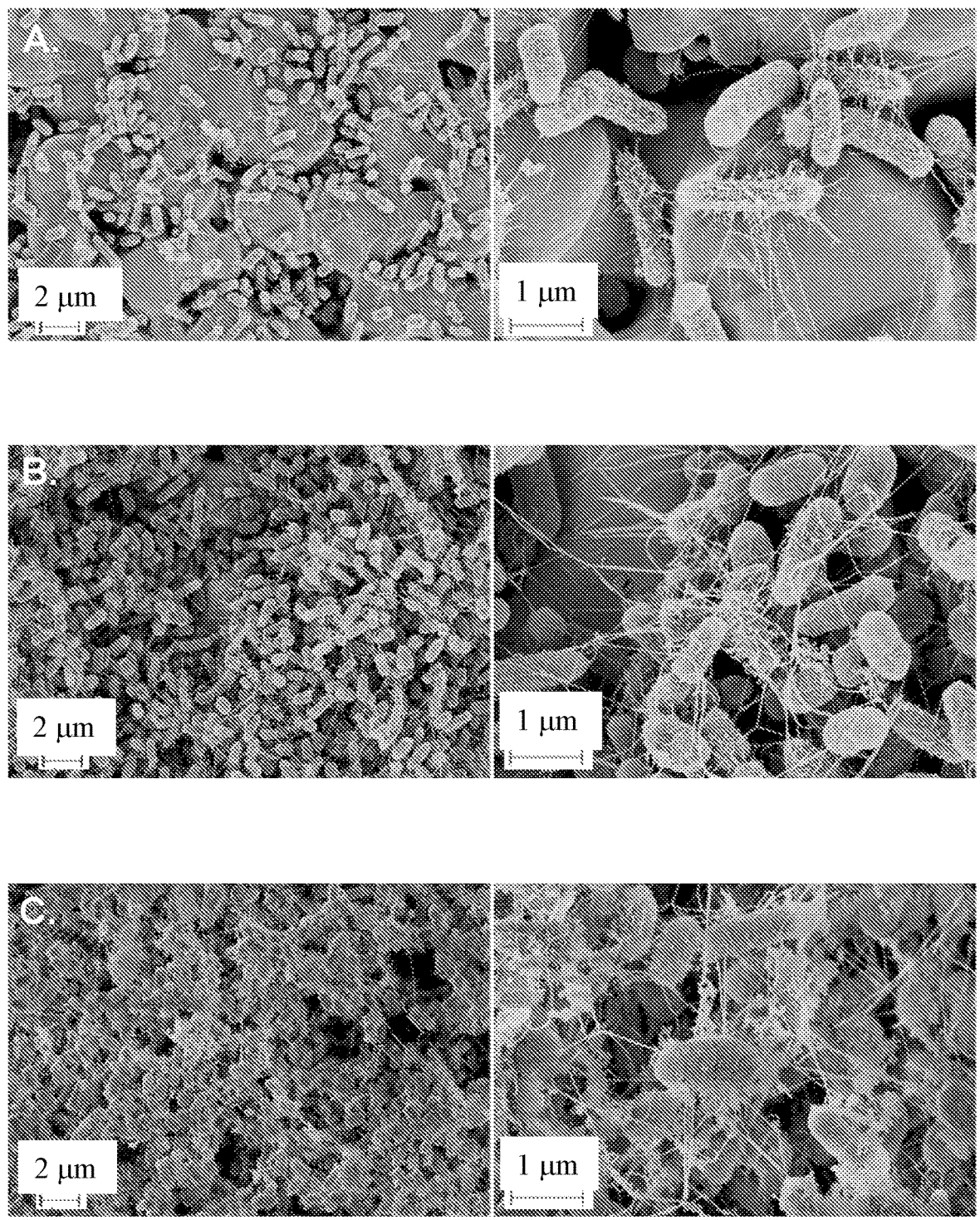
FIG. 5. Scanning electron micrographs showing the effect of ExPEC solution (A), PAC with ExPEC solution (B), and PAC-DMAC with ExPEC solution (C) after the agglutination assay.
Figure 6:
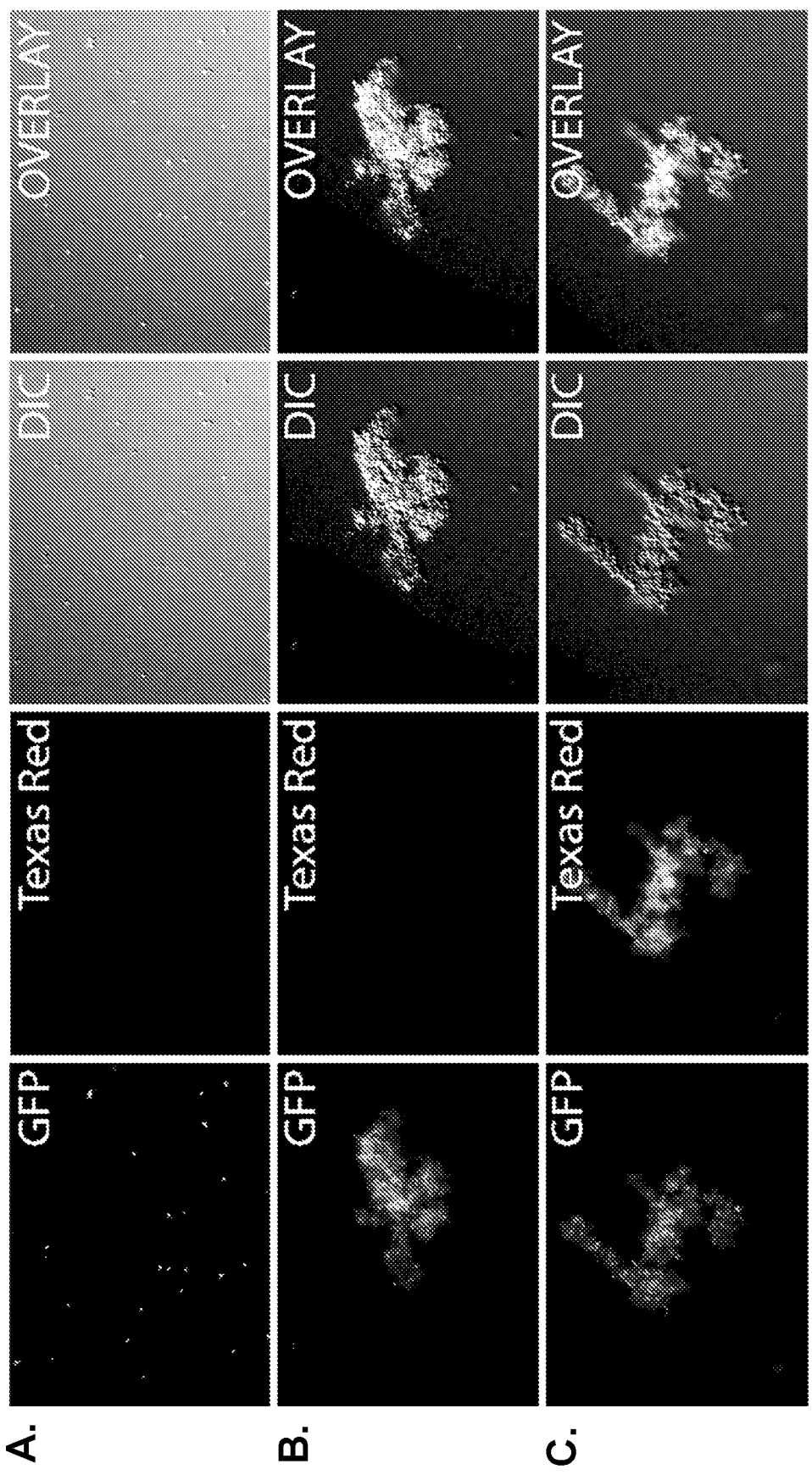
FIG. 6. Micrographs of the in vitro agglutination assay containing the ExPEC solution (A), PAC and ExPEC solution (B), and PAC-DMAC with ExPEC solution (C) under a magnification of 40×. Micrographs were obtained using the green fluorescent protein (GFP) and Texas Red filters, and the differential interference contrast (DIC) microscopy.

Scanning electron micrographs of ExPEC solution, PAC with ExPEC solution, and PAC-DMAC with ExPEC solution were used to visualize the interaction between PAC-DMAC and ExPEC after the agglutination assay. FIG. 5A shows the normal physical structure of the fimbriae-like structures expressed by ExPEC. FIG. 5B shows the interaction of PAC with ExPEC. This micrograph indicates that PAC interact with the fimbriae-like structures on the surface of the bacteria, which allows the formation of bacteria-to-bacteria agglomerates, thus causing agglutination and precipitation of the bacteria. FIG. 5C shows the interaction of PAC-DMAC with ExPEC. This micrograph indicates that PAC-DMAC have higher affinity with the fimbriae-like structures on the surface of the bacteria, thus causing higher agglutination and precipitation of the bacteria as was demonstrated previously by the agglutination assay.

Visualization of the interaction between proanthocyanidin and extra-intestinal pathogenic *Escherichia coli* during in-vitro and in-vivo agglutination by fluorescent microscopy. Fluorescent and differential interference contrast (DIC) microscopy was performed on the precipitated material of ExPEC, PAC with ExPEC, and PAC-DMAC with ExPEC from the in vitro agglutination assay. FIG. 6A show that ExPEC were detected using the GFP filter and were visible by DIC microscopy but were not detected with the Texas Red filter. The overlay of GFP, Texas Red, and DIC micrographs only demonstrated GFP expression from ExPEC, which were dispersed across the field of view. FIG. 6B show that PAC were not detected with the GFP and Texas Red filters, but ExPEC were detected with the GFP filter and were visible by DIC microscopy. The overlay of GFP, Texas Red, and DIC micrographs only demonstrated GFP fluorescence from ExPEC. Unlike FIG. 6A in which ExPEC alone were dispersed across the field of view, FIG. 6B shows that when ExPEC are instilled with PAC the ExPEC are located in clumps on the slide because the ExPEC are closely associated with PAC. However, the PAC are not visible by fluorescent microscopy because PAC were not fluorescently tagged. FIG. 6C show that PAC-DMAC were detected with the Texas Red filter and that ExPEC were detected with the GFP filter and with DIC microscopy. The overlay of GFP, Texas Red, and DIC micrographs demonstrated GFP expression from ExPEC and fluorescence of PAC-DMAC with the Texas Red filter. Micrograph suggests that PAC-DMAC were entrapping ExPEC in a web-like network, thus demonstrating agglutination of ExPEC by PAC-DMAC. Evidence of colocalization can be observed by the yellow color produced upon overlaying the red (Texas Red) and green (GFP) filters.

Figure 7:
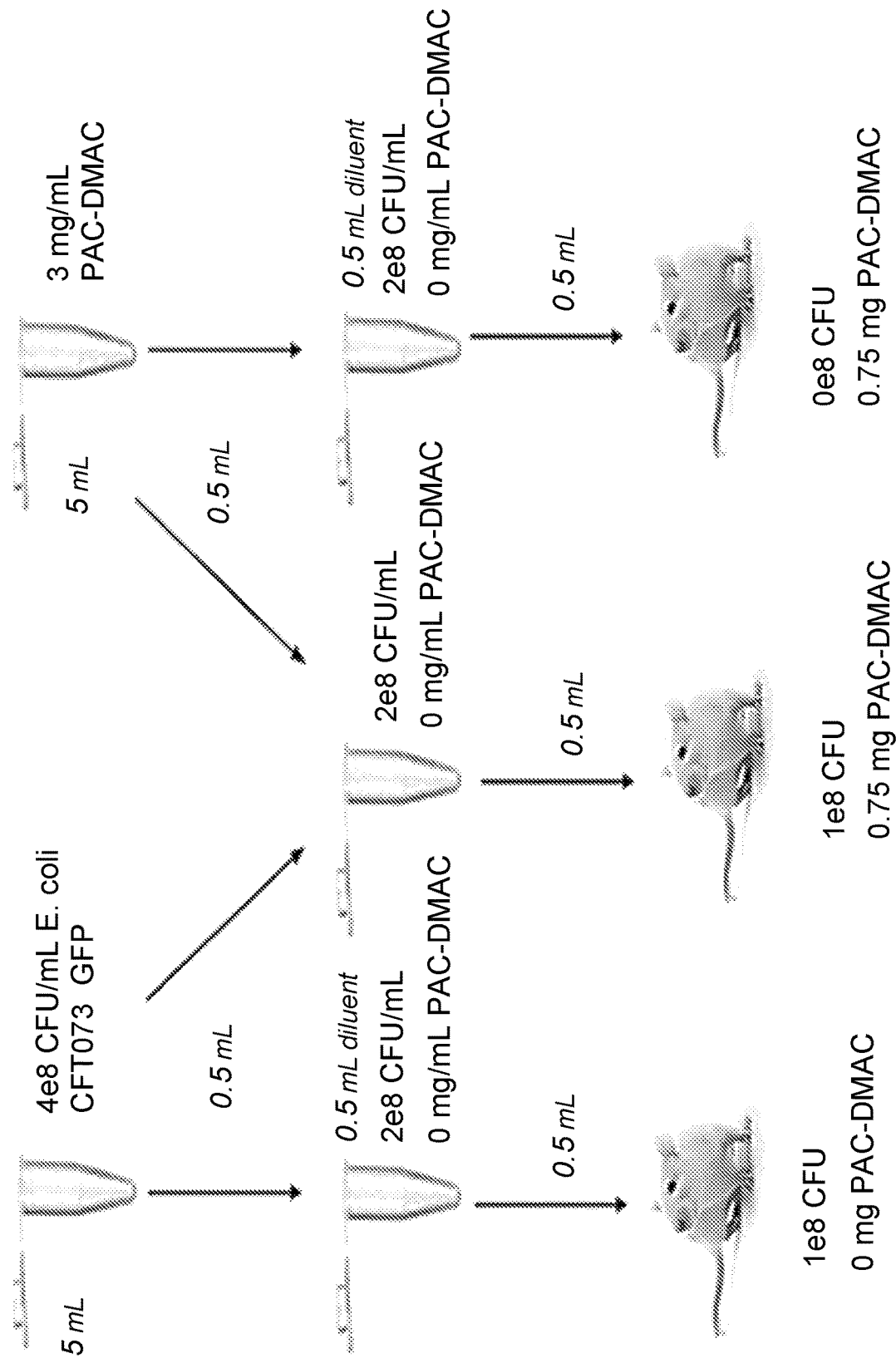
FIG. 7. Schematic diagram of experimental design and preparation of solutions.
Figure 8:
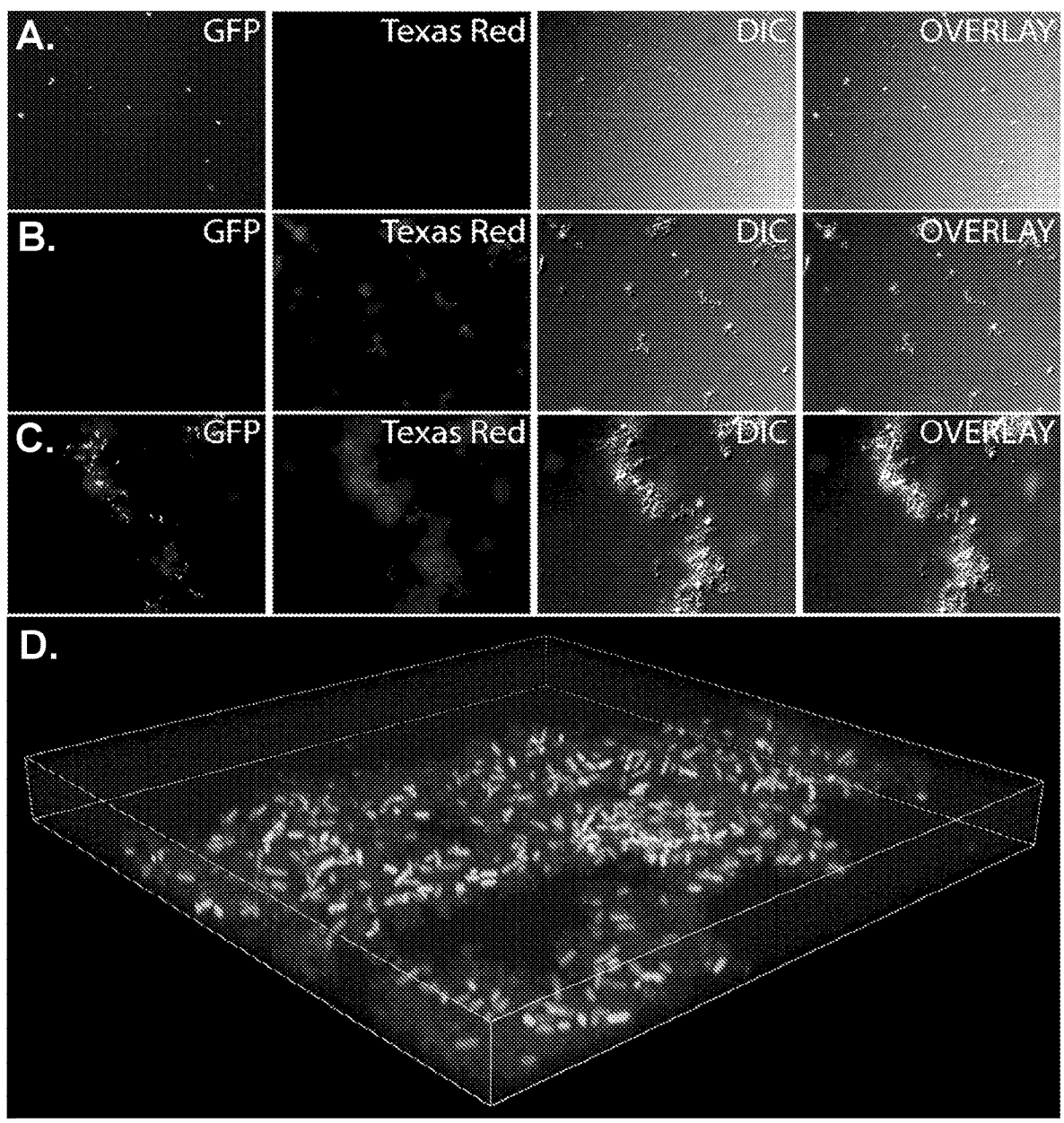
FIG. 8. Micrographs of rat urine containing the ExPEC (A), PAC-DMAC (B), and PAC-DMAC with ExPEC (C) under a magnification of 40×. Micrographs were obtained using the green fluorescent protein (GFP) and Texas Red filters, and the differential interference contrast (DIC) microscopy. Laser scanning confocal micrograph of rat urine containing PAC-DMAC with ExPEC solution (D) under a magnification of 100×.

Similarly, fluorescent and DIC microscopy was performed on the urine samples of rats that were subjected to intra-vesicular bladder administration of ExPEC, PAC-DMAC, and PAC-DMAC with ExPEC (FIG. 7). FIG. 8A show that ExPEC were detected with the GFP filter and were visible by DIC microscopy. The ExPEC were not detected with the Texas Red filter. FIG. 8B show that PAC-DMAC were not detected with the GFP filter but are detected with the Texas Red filter. While no ExPEC were instilled in this treatment, the DIC microscopy shows a number of distinct white spots that could be bacteria that were native to the rat urine/bladder. We have observed that rats have an endogenous bacterial population in their urine/bladder. The overlay of GFP, Texas Red, and DIC micrographs indicate that PAC-DMAC are closely associated with the suspected endogenous bacteria, indicating that PAC may be entrapping endogenous bacteria. FIG. 8C show that ExPEC were detected with the GFP filter and PAC-DMAC were detected with the Texas Red filter. The overlay of GFP, Texas Red, and DIC micrographs indicate that PAC-DMAC were entrapping ExPEC. The slide containing PAC-DMAC with ExPEC solution was later observed using fluorescent confocal microscopy (FIG. 8D). Confocal microscopy captures 2D-images at different depths allowing the reconstruction of 3D-images. The micrograph of PAC-DMAC with ExPEC supports our finding that PAC-DMAC (red color) entangle ExPEC (green color). This is distinctly evident where yellow color was detected, which is produced by the overlapping of the Texas red and GFP filters. The laser scanning confocal micrograph illustrates that PAC-DMAC is localized where ExPEC are localized. This co-localization is the result of the bacterial agglutination, which corresponds to an increase in concentration of bacteria in a limited area of the micrograph. This phenomenon may inhibit bacterial growth, cause structural damage to bacteria, and increase bacterial clearance by macrophages and other phagocytic cells. In addition, the bacterial agglutination leads to a decrease in enterocyte invasion by ExPEC.

Conclusion. In this work, we described the condensation reactions between PAC with cinnamaldehydes to obtain FP. MALDI-TOF MS, used to characterized FP, showed that PAC and cinnamaldehydes were covalently linked. Spectrophotometric analysis indicate that FP exhibit fluorescence at useful wavelengths for use in fluorescent microscopy. FP were used to visualize PAC bioactivity. Our results suggested that FP did not affect PAC agglutination activity. On the contrary, FP were significantly more bioactive (p-value<0.05) for agglutinating ExPEC compared to PAC at a fixed concentration of 200 µg/mL of PAC equivalent. Fluorescent micrographs of PAC-DMAC demonstrated the ability of FP to visualize the in-vitro agglutination of ExPEC. These results suggest that FP is a more cost-effective alternative for visualizing the temporal interaction of PAC as compared to the complex and expensive technique of $^{14}C$ radio-labeling of PAC. Future work should include the use of FP to study the in situ and in vivo interaction of PAC with endogenous bacteria and in the development of a diagnostic tool for determining bacteriuria and urinary tract infections (UTIs) in real-time. Currently, the diagnosis of bacteriuria and UTIs are performed using urinalysis and culture test, which can take up to two days to reveal infection status.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered orally, intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage.

The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antibacterial agents and have higher potency and/or reduced toxicity as compared to naturally occurring proanthocyanidins. Preferably, compounds of the invention are more potent and less toxic than naturally occurring proanthocyanidins, and/or avoid a potential site of catabolic metabolism encountered with naturally occurring proanthocyanidins, i.e., have a different metabolic profile than naturally occurring proanthocyanidins.

The invention provides therapeutic methods of treating bacterial infections in a mammal, which involve administering to a mammal having a bacterial infection an effective amount of a compound or composition described herein. A mammal includes a primate, human, rodent, canine, feline, bovine, ovine, equine, swine, caprine, bovine and the like.

The ability of a compound of the invention to treat bacterial infections may be determined by using assays well known to the art. For example, the design of treatment protocols, toxicity evaluation, data analysis, quantification of bacterial cell kill. In addition, ability of a compound to treat bacterial infections may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Material and Methods

Chemical and materials. Cinnamaldehyde (CIN), 4-methylcinnamaldehyde (TOL), 4-(dimethylamino)cinnamaldehyde (DMAC), 4-hydroxy-3,5-dimethoxycinnamaldehyde (SIN), 4-hydroxy-3-methoxycinnamaldehyde (CON), 2,5-dihydroxybenzoic acid (DHB), magnesium chloride, bradykinin, glucagon, chitosan, sodium triphosphate, and Triton X-100 were obtained from Sigma-Aldrich (Milwaukee, WI, USA). Methanol, acetone, water, sodium hydroxide, hydrochloric acid, Dulbecco's phosphate buffered saline solution 10× with calcium and magnesium (PBS Ca$^{+2}$/Mg$^{+2}$), Fluoromount-G, and HyperSep C$_{18}$ cartridges (5 g bed weight, 25 mL column volume, 40-60 µm particle size, 60 Å pore size) were purchased from Fisher Scientific (Fair Lawn, NJ, USA). Dulbecco's phosphate buffered saline solution (PBS) was diluted to 1× concentration before use. Ethanol (100%) was obtained from Decon's lab (King of Prussia, PA, USA). Sephadex LH-20® (18-111 µm particle size) was purchased from GE Healthcare (Uppsala, Sweden). Cranberry fruits were obtained from Habelman Bros. Company (Tomah, WI, USA)

Extraction of proanthocyanidins. Whole frozen cranberries were placed in liquid nitrogen and blended into a powder. Two liters of acetone 70% (v/v) were added to 1 kg of frozen cranberry powder and sonicated for 30 minutes. The acetone was removed using rotary evaporation. The aqueous extract (~500 mL) was filtered with Whatman 1, Whatman 50, and a Corning funnel with pores of 0.22 µm. The filtered aqueous cranberry extract was loaded onto an FPX-66 resin that was previously washed with ethanol and water. Polyphenols were purified by sequential elution with water and ethanol. The ethanol fraction was concentrated (~25 mL) by rotary evaporator and loaded onto a Sephadex LH-20 resin that was previously swollen in water and equilibrated with ethanol for 45 min at 4 mL/min. PAC were purified by sequential elution with ethanol, ethanol/methanol (1:1), and acetone 80% (v/v). The acetone fraction contained PAC. The acetone was removed by rotary evaporation, lyophilized, and stored at −20° C.

Synthesis of proanthocyanidin-cinnamaldehydes pyrylium products. Proanthocyanidins (50 mg) were dissolved in 2 mL of methanol and mixed with 5 mg of magnesium chloride. Each cinnamaldehyde compounds (6 mg) were added, followed by 250 µL of HCl (0.3 M). After 60 minutes of incubation at 25° C., the reaction was quenched by adding 250 µL of NaOH (0.3 M). The pH of the quenched reaction was checked using pH strips until a neutral pH was obtained. Then, 6 mL of water were added to each neutralized solution prior to isolation of products.

Fluorescent PAC products can be synthesized at 25° C., pH 3, and for 60 minutes. Also, these products can be obtained at a higher temperature (25-100° C.), pH (1-4), and longer incubation times. The PAC-cinnamaldehydes weight ratios may vary in the reactions.

Purification of proanthocyanidin-cinnamaldehydes pyrylium products. The purification of FP was achieved using two procedures. The first procedure to purify PAC-CIN, PAC-TOL, PAC-CON, and PAC-SIN was carried out using Sephadex LH-20®, whereas the second procedure to purify PAC-DMAC was carried out using a C$_{18}$ cartridge. For the first procedure: the neutralized solutions (PAC-CIN, PAC-TOL, PAC-CON and PAC-SIN) were loaded onto a glass column (Kontes, 2.5 cm internal diameter×20 cm length) packed with Sephadex LH-20® that was previously conditioned with water and equilibrated with ethanol. Unreacted cinnamaldehydes were eluted with ethanol, and the FP were eluted with acetone 80% (v/v). The fractions of FP were concentrated by evaporating the acetone and lyophilizing. For the second procedure, the neutralized sample of PAC-DMAC was loaded onto a C$_{18}$ cartridge that was previously conditioned with methanol followed by double distilled water. Unreacted DMAC was eluted with water, and the PAC-DMAC fraction was eluted with methanol 45% (v/v). The PAC-DMAC products were obtained by evaporation of the methanol followed by lyophilization.

Matrix-assisted laser desorption/ionization time-of-flight mass spectrometry. Matrix-assisted laser desorption/ionization time-of-flight mass spectrometry (MALDI-TOF MS) spectra were collected on a Bruker UltraFlex III mass spectrometer (Billerica, MA, USA). All analyses were performed in positive reflectron mode. Deflection was set at 800 Da. Samples (2 mg/L of PAC equivalent in methanol) and matrix (DHB; 0.973 mM in methanol) were mixed at a 1:1 volume ratio and spotted on the MALDI-TOF MS stainless steel target (0.3 µL). Spectra were calibrated with bradykinin (1060.6 Da) and glucagon (3483.8 Da) as external standards. FP were detected as pyrylium ions $[M]^+$, whereas non-charged conjugates of cinnamaldehydes and PAC were detected as sodium adducts $[M+Na]^+$. FlexControl and FlexAnalysis (Bruker Daltonik GmbH, Bremen, Germany) were used for data acquisition and data processing, respectively.

Absorption and emission spectra of proanthocyanidin-cinnamaldehyde pyrylium products. The absorption spectra for PAC and FP were acquired using a UV/Visible spectrometer (Varian Cary50) in the spectral range 250-700 nm by dissolving the samples in methanol. The concentrations were adjusted so that the absorption intensities of the samples were similar. The fluorescence emission spectra were acquired using a spectrofluorimeter (Hitachi f-4500) at the previously determined maximum wavelength ($\lambda$) absorption. The slits for excitation and emission were both set at 5 nm and the excitation voltage at 700 V.

Figure 9:
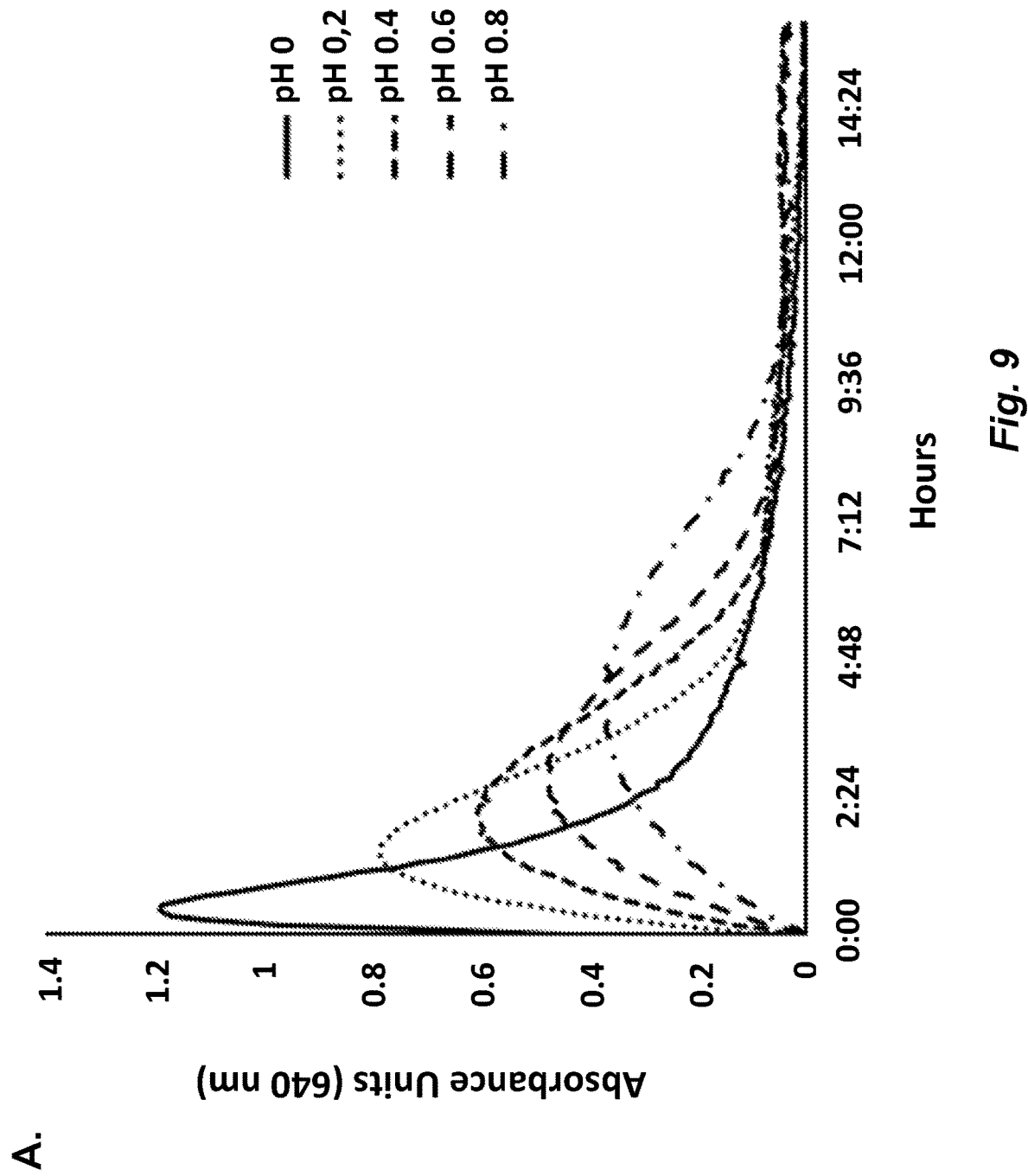
FIG. 9. Graph showing pH of the reaction has a large effect on absorbance at 640 nm (A). For procyanidin A2 at a low pH, the reaction is rapid, but the maximum absorbance is delayed to over 4.5 hours at a pH of 0.8. Acid is a catalyst to generate the DMAC carbocation that reacts with the terminal C8 position of PACs to form the initial condensation product. In contrast, the effect of pH on rate and maximum absorbance at 559 nm is much lower than for 640 nm (B), which suggests separate reactions occur over a longer time frame to form the more stable chromophores. The dehydration of the initial condensation product to form the stable open ring cation and the subsequent oxidation to from the pyrylium cation may occur over a longer timeframe. Indeed, the condensation reaction of cinnamaldehyde with catechin occurs by heating the reaction mixture at 100° C. for 50 minutes without acid and the reaction with procyanidin B1 occurs in the dark at room temperature after 8 days, again without acid (J. of Agricultural and Food Chemistry, 2008, 56, 5864).
Figure 9:
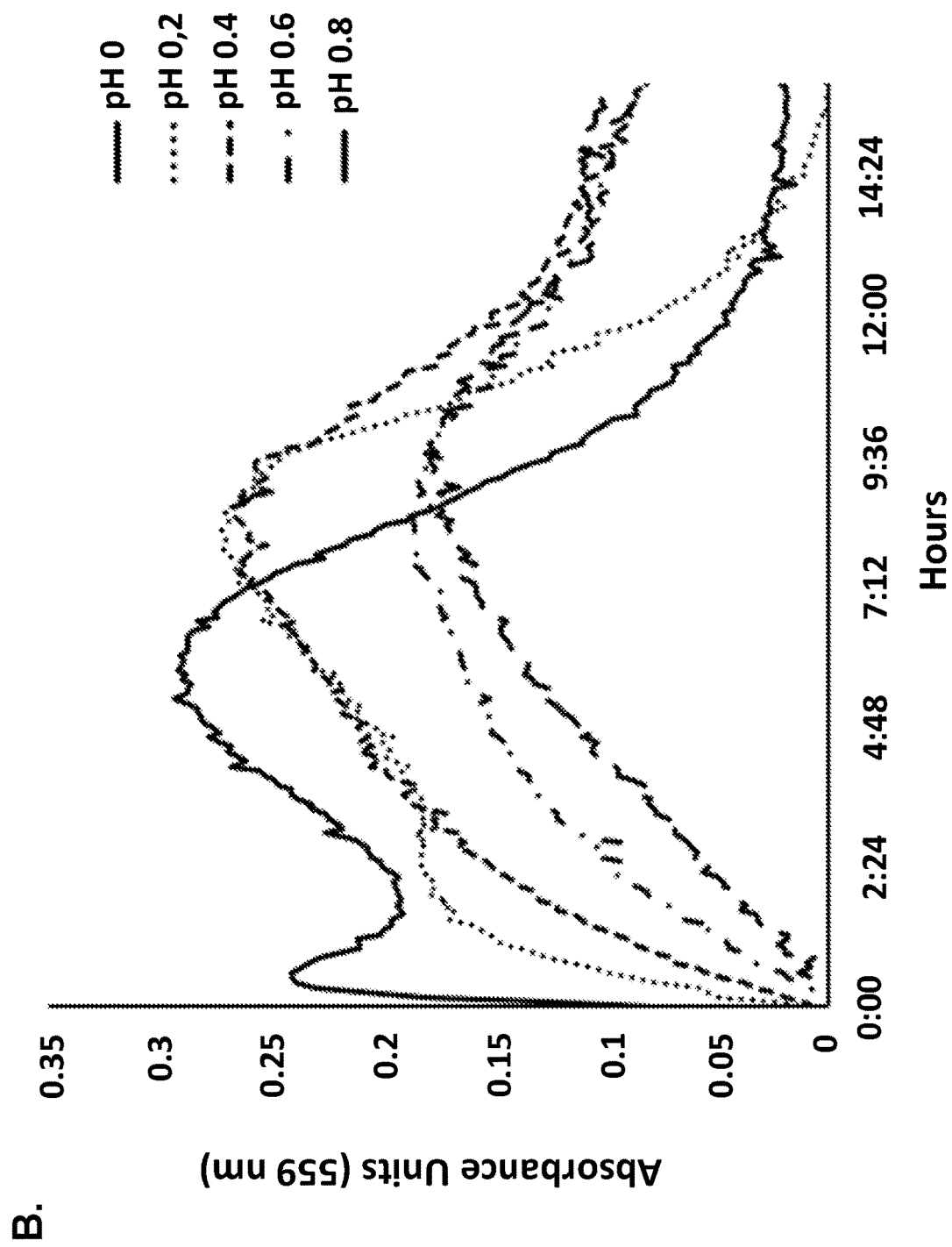

Characterization of proanthocyanidin and 4-(dimethylamino)cinnamaldehyde reaction product (DMAC) (see FIG. 9). The DMAC reaction products with PAC have two absorption maximum wavelength absorptions at 276 and 559 nm. The DMAC reaction product with PAC resulted in a stable purple color. When a fluorescence emission spectrum was acquired using a fluorimeter at the excitation wavelength of 559 nm, we discovered that the DMAC reaction products with PAC exhibit fluorescence at 613 nm. We also reacted four other cinnamaldehydes (cinnamaldehyde, 4-methylcinnamaldehyde, 4-hydroxy-3-methoxycinnamaldehyde, and 4-hydroxy-3,5-dimethoxycinnamaldehyde) with PACs in order to study the spectral properties of the reaction products in comparison to the DMAC products. Reaction products between these cinnamaldehydes and PACs produced unique compounds with different and useful absorption and emission wavelengths. For instance, the product of the reaction between (1) cinnamaldehyde with PACs exhibited a maximum absorption at 404 nm and a maximum emission at 473 nm, (2) 4-methylcinnamaldehyde with PACs exhibited a maximum absorption at 416 nm and a maximum emission at 480 nm, (3) 4-hydroxy-3-methoxycinnamaldehyde with PACs exhibited a maximum absorption at 443 nm and a maximum emission at 524 nm, and (4) 4-hydroxy-3,5-dimethoxycinnamaldehyde with PAC exhibited a maximum absorption at 460 nm and a maximum emission at 536 nm. Apart from these spectroscopy characteristics, we determine that these PAC-cinnamaldehyde compounds have greater bioactivity than PACs alone to agglutinate extra-intestinal pathogenic *Escherichia coli* (ExPEC).

Example 2. Bioactivity Assays

In vitro agglutination assay. ExPEC strain CFT073, transformed to expresses green fluorescent protein (GFP), was cultured under static conditions in tryptose broth for 48 h at 37° C. After the incubation time, 1 mL of the culture was taken from the surface of the culture to inoculate a new culture under static conditions for 24 h at 37° C. On the day of assay, the culture was centrifuged at 1800 g for 10 min to obtain a bacterial pellet. The pellet was washed twice with PBS by centrifugation at 1840 g for 10 min and then resuspended in 1 mL PBS to obtain the bacterial stock solution. Optical density was used to adjust the bacterial cell density with a previously established bacterial density-absorbance curve. The assay was conducted in 3.0 mL microcuvettes using 1.0 mL total reaction volume. Nine hundred and forty microliters of PBS were added to each microcuvette. This was followed by 10 µL of PAC and FP at a concentration of 20 mg/mL of PAC equivalent, and 50 µL of ExPEC stock solution at $1.0e^{10}$ CFU/mL. Transmittance was read at 600 nm every 1 min for 4 hours on a UV/Visible spectrometer (Evolution 201, Thermo Scientific). The area under the curve for each sample was calculated as a function of the ability of PAC and FP to agglutinate ExPEC.

Scanning electron microscopy. The agglutinated ExPEC obtained from the in vitro agglutination assay was passed through a 0.45 µm silver membrane filter (Steritech #45329), followed by treatment with 1 mL of glutaraldehyde (3% v/v) to fix the bacteria. The silver membrane filter was left in glutaraldehyde (3% v/v) overnight. The filter was then dehydrated with 15-minute treatments with a series of increasing ethanol concentrations in doubly distilled water (v/v): 30, 50, 70, 80, 90, 95, and two-times with absolute ethanol. Then, the filter was dried via the critical point procedure (10 minutes×3 soaks) and adhered to aluminum SEM specimen stubs with double-sided carbon sticky tabs. The filter was then sputter coated with a ~5 nm layer of gold. Scanning electron microscopy images were acquired with a Zeiss LEO-1550 VP (Zeiss, Oberkochen, Germany) using an accelerating voltage at 6 kV.

In vivo urine agglutination experiment. Sprague-Dawley rats (Charles River Laboratories, Wilmington, MA) weighing 220 to 240 g (10-weeks old) were separated into three groups and acclimated for 10 days prior to the day of the experiment (FIG. 7). Rats were kept under circadian rhythm with unlimited access to water and chow and monitored daily for symptoms of stress and discomfort. The first group was treated with ExPEC solution at a final concentration of $1.0e^{8}$ CFU/mL. The second group was treated with PAC-DMAC at a final concentration of 750 µg. The third group was treated with PAC-DMAC at a final concentration of 750 µg and ExPEC solution at a final concentration of $1.0e^{8}$ CFU/mL. On the day of the experiment, rats were anesthetized with isoflurane (4%) and oxygen in a closed box and maintained on isoflurane (1-2.5%) and oxygen administered by nose-cone. After anesthesia, rats were subjected to one of the three treatments (ExPEC, PAC-DMAC, and PAC-DMAC with ExPEC) by intra-vesicular bladder administration via a catheter. The catheter remained in place for the duration of the experiment (90 min) to prevent voiding of the bladder. After 90 min of incubation, urine from each rat was collected via the catheter and place into a collection tube. This experimental procedure was approved by the Institutional Animal Care and Use Committee (IACUC) at the University of Wisconsin-Madison (Protocol #A005854-A03).

Agglutination fluorescent images. Samples from the in vitro and in vivo agglutination assays were centrifuged at 1800 g for 10 min. The supernatants were discarded, and the pellets were suspended in 1 mL of neutral buffered formalin and stored for 1 h at 4° C. Next, 50 µL of the suspensions were spotted onto glass slides that were previously spotted with 50 μL of Fluoromount-G solution and then covered with coverslips. For the in vitro agglutination assays, the slides evaluated were the treatments containing ExPEC, PAC with ExPEC, and PAC-DMAC with ExPEC. For the in vivo agglutination assay, the slides evaluated were the treatments containing ExPEC, PAC-DMAC, and PAC-DMAC with ExPEC. Both in vitro and in vivo agglutination images were acquired under a Zeiss Axio Imager M2 Microscope using the differential interference contrast (DIC), and green fluorescent protein (GFP) and Texas red filters. In addition, 3D-images of PAC-DMAC with ExPEC solution was acquired using a Nikon A1R-SI+ confocal microscope at a magnification of 100×.

Statistical analysis. Data were analyzed using RStudio (version 1.2.1335) by the 'car' and 'agricolae' packages. One-way analysis of variance with least significant difference (LSD) post-test were used for multiple comparisons with a probability of less than 0.05 considered to be statistically significant.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
| --- | --- |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
| --- | --- |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/mL) | mg/ml |
| --- | --- |
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1 N Sodium hydroxide solution (pH adjustment to 7.0-7.5) | q.s. |
| Water for injection | q.s. ad 1 mL |

| (vi) Aerosol | mg/can |
| --- | --- |
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
| --- | --- |
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
| --- | --- |
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
| --- | --- |
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
| --- | --- |
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
| --- | --- |
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A proanthocyanidin condensation product comprising three or more monomers, wherein each monomer of the three or more monomers is independently selected from the group consisting of Formulas S1, S2, S3, S4, S5 and pyrylium cations thereof:

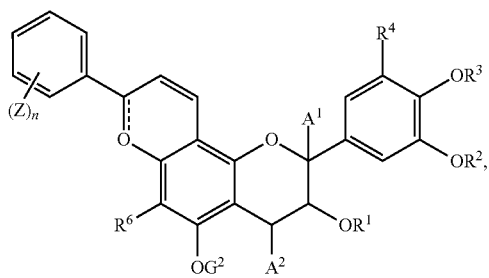
(S1)

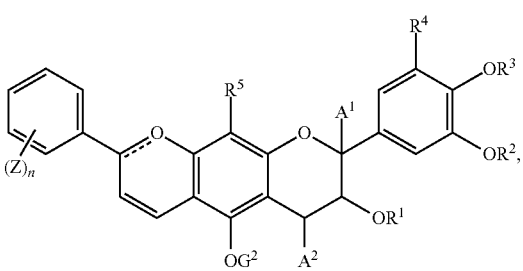
(S2)

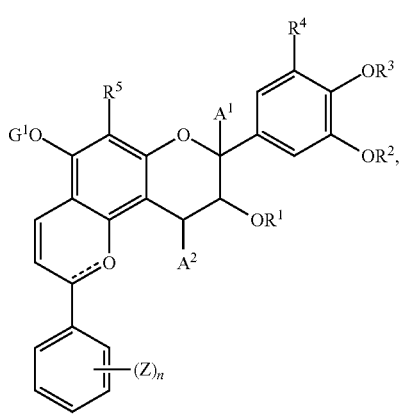
(S3)

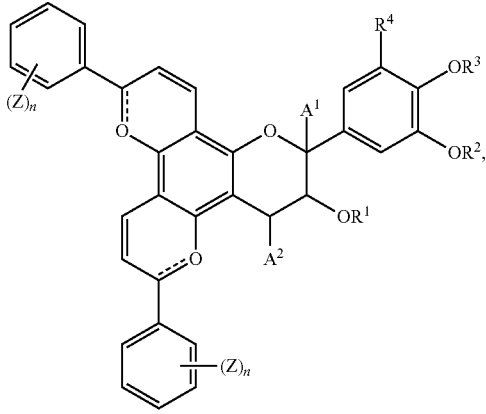
(S4)

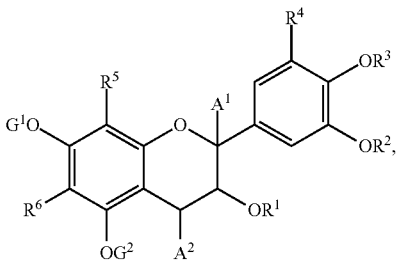
(S5)

wherein
- - - - - represents a single or double bond wherein a pyrylium cation at oxygen (O$^+$) is formed when - - - - - is a double bond;

$A^1$ and $A^2$ are each independently radical or H;

$G^1$ is radical, H, —(C$_1$-C$_6$)alkyl, or —C(=O)(C$_1$-C$_6$)alkyl;

$G^2$ is H, —(C$_1$-C$_6$)alkyl, or —C(=O)(C$_1$-C$_6$)alkyl;

$R^1$, $R^2$ and $R^3$ are each independently H, —(C$_1$-C$_6$)alkyl, or —C(=O)(C$_1$-C$_6$)alkyl;

$R^4$ is H or OR$^a$ wherein R$^a$ is H, —(C$_1$-C$_6$)alkyl or —C(=O)(C$_1$-C$_6$)alkyl;

$R^5$ and $R^6$ are each independently radical or H;

each Z is independently halo, —(C$_1$-C$_6$)alkyl, OR$^b$, or N(R$^b$)$_2$, wherein each R$^b$ is independently H, —(C$_1$-C$_6$)alkyl, or —C(=O)(C$_1$-C$_6$)alkyl; and each n is independently 0-5;

wherein an A-type linkage between a first monomer and a second monomer is formed when $A^1$ and $A^2$ of the first monomer are radical, $G^1$ and $R^5$ of the second monomer are radical, $A^1$ and $G^1$ form a bond, and $A^2$ and $R^5$ form a second bond; or a B-type linkage between the first monomer and the second monomer is formed when $A^2$ of the first monomer is radical, $R^5$ or $R^6$ of the second monomer is radical, and $A^2$ and $R^5$ form a bond or $A^2$ and $R^6$ form a bond;

wherein the first monomer is a monomer of Formulas S1 to S4 and the second monomer is a monomer of Formula S2, S3 or S5, and the product is an oligomer having a degree of polymerization of three or more.

2. The product of claim 1 wherein the product comprises the A-type and B-type linkage.

3. The product of claim 1 wherein the product has the A-type linkage between the first monomer and the second monomer.

4. The product of claim 1 wherein $R^4$ is H.

5. The product of claim 1 wherein $R^1$, $R^2$ and $R^3$ are H.

6. The product of claim 1 wherein the product is capable of fluorescence and has an absorption maximum wavelength of about 350 nanometers to about 600 nanometers or the product has an emission maximum wavelength of about 450 nanometers to about 650 nanometers.

7. A composition comprising the proanthocyanidin condensation product according to claim 1 and at least one other proanthocyanidin.

* * * * *